(12) United States Patent
Matsui et al.

(10) Patent No.: US 7,871,806 B2
(45) Date of Patent: *Jan. 18, 2011

(54) ASPARAGINASES

(75) Inventors: Tomoko Matsui, Chiba (JP); Esben Peter Friis, Herlev (DK); Akihiko Yamagishi, Tokyo (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/782,150

(22) Filed: May 18, 2010

(65) Prior Publication Data

US 2010/0221385 A1    Sep. 2, 2010

Related U.S. Application Data

(60) Continuation of application No. 12/613,983, filed on Nov. 6, 2009, which is a division of application No. 12/044,055, filed on Mar. 7, 2008, now Pat. No. 7,666,652.

(60) Provisional application No. 60/894,316, filed on Mar. 12, 2007.

(30) Foreign Application Priority Data

Mar. 9, 2007    (EP)    .................... 07103862

(51) Int. Cl.
*C12N 9/82* (2006.01)
*C12N 1/20* (2006.01)
*C12N 1/00* (2006.01)
*C12N 15/00* (2006.01)
*C07H 21/04* (2006.01)

(52) U.S. Cl. ............... 435/229; 435/252.3; 435/254.11; 435/254.3; 435/320.1; 426/49; 536/23.2; 536/23.1

(58) Field of Classification Search ................... None
See application file for complete search history.

(56) References Cited

FOREIGN PATENT DOCUMENTS

| EP | 1 704 782 | 9/2006 |
|---|---|---|
| WO | WO2004/026042 | 4/2004 |
| WO | WO2004/030468 | 4/2004 |
| WO | WO2004/032648 | 4/2004 |

OTHER PUBLICATIONS

Lubkowski et al, "Atomic resolution structure of *Erwinia chrysanthemi* L-asparaginase", Acta Cryst. D, vol. 59, pp. 84-92 (2003).
Watanabe K. et al, "Designing Thermostable Proteins: Ancestral Mutants of 3-Isopropylmalate Dehydrogenase Designed by using a Phylogenetic Tree", Journal of Molecular Biology, vol. 335, pp. 664-674 (2006).
Kotzia et al, Journal of Biotechnology, vol. 119, pp. 309-323 (2005).
Liu et al, Protein Engineering, vol. 16, No. 1, pp. 19-25 (2003).

*Primary Examiner*—Nashaat T Nashed
(74) *Attorney, Agent, or Firm*—Kristin J. McNamara

(57) ABSTRACT

The invention relates to new asparaginases having improved properties, preferably improved thermotolerance, such as improved activity at high temperatures and/or improved thermostability. The invention also relates to DNA sequences encoding such improved asparaginases, their production in a recombinant host cell, as well as methods of using the asparaginases, in particular for reduction of acrylamide in foods. The invention furthermore relates to methods of generating and preparing asparaginase variants having improved properties.

26 Claims, 4 Drawing Sheets

Alignment of asparaginases from 6 eukaryotic species

| SEQ ID NO: 1 | Asparaginase | Aspergillus oryzae |
| SEQ ID NO: 2 | Asparaginase | Aspergillus niger |
| SEQ ID NO: 3 | Asparaginase | Aspergillus fumigatus |
| SEQ ID NO: 4 | Asparaginase | Aspergillus nidulans |
| SEQ ID NO: 5 | Asparaginase | Penicillium citrinum |
| SEQ ID NO: 6 | Asparaginase | Aspergillus terreus |

```
SEQ ID NO: 5       -MRLLFNTLAVSALAATSYASPIIHSRA---SNTSY--TNSNGLKFNHFDASLPNVTLLA
SEQ ID NO: 2       ---MPLKPILLSALASLASASPLLYSRT---TNETFVFTNANGLNFTQMNTTLPNVTIFA
SEQ ID NO: 4       -MGLRVKALAVAALATLSQASPVLYTREDTTSNTTYAFTNSNGLNFTQMNTTLPNVTIFA
SEQ ID NO: 1       -MGVNFKVLALSALATISHASPLLYPRA-TDSNVTYVFTNPNGLNFTQMNTTLPNVTIFA
SEQ ID NO: 3       MTKLSFKIITLAAMIAVGNASPFVYPRA-TSPNSTYVFTNSHGLNFTQMNTTLPNVTILA
SEQ ID NO: 6       -MGFNIKALTVAALAALGHASPL-YSRA--DANVTYVFTNAHGLNFTQMNTTLPNVTILA

SEQ ID NO: 5       TGGTIAGTSDDKTATAGYESGALGINKILSGIPEVYDIANVNAVQFDNVNSGDVSSSLLL
SEQ ID NO: 2       TGGTIAGSDSSSTATTGYTSGAVGVLSLIDAVPSMLDVANVAGVQVANVGSEDITSDILI
SEQ ID NO: 4       TGGTIAGSAASNTATTGYQAGALGIQTLIDAVPEMLSVANIAGVQISNVGSPDVTSTILL
SEQ ID NO: 1       TGGTIAGSSADNTATTGYKAGAVGIQTLIDAVPEMLNVANVAGVQVTNVGSPDITSDILL
SEQ ID NO: 3       TGGTIAGSSNDNTATTGYTAGAIGIQQLMDAVPEMLDVANVAGIQVANVGSPDVTSSLLL
SEQ ID NO: 6       TGGTIAGSSADNTATTGYKAGAIGIQQLIDAVPEMLNVANVAGVQVTNVGSPDVTSHILL

SEQ ID NO: 5       NMTHTLQKTVCDDPTISGAVITHGTDTLEESAFFIDATVNCGKPIVFVGSMRPSTAISAD
SEQ ID NO: 2       SMSKKLNRVVCEDPTMAGAVITHGTDTLEETAFFLDATVNCGKPIVIVGAMRPSTAISAD
SEQ ID NO: 4       EMAHRLNKVVCEDPSMAGAVVTHGTDTLEETAFFLDATVNCGKPIVIVGAMRPATAISAD
SEQ ID NO: 1       RLSKQINEVVCNDPTMAGAVVTHGTDTLEESAFFLDATVNCRKPVVIVGAMRPSTAISAD
SEQ ID NO: 3       HMARTINEVVCDDPTMSGAVITHGTDTLEETAFFLDATVNCGKPIVVVGAMRPATAISAD
SEQ ID NO: 6       DMVRMLDELVCQDETMAGAVITHGTDTLEETAFFLDATMPCRKPVVVVGAMRPSTAISAD

SEQ ID NO: 5       GPMNLLQGVTVAADKQAKNRGALVVLNDRIVSAFFATKTNANTMDTFKAYEQGSLGMIVS
SEQ ID NO: 2       GPFNLLEAVTVAASTSARDRCAMVVMNDRIASAYYVTKTNANTMDTFKAMEMCYLCEMIS
SEQ ID NO: 4       GPYNLLQAVTVASTKEARNRGAMVVMNDRIASAYYVSKTNANTMDTFKAVEMGYLGAIIS
SEQ ID NO: 1       GPLNLLQSVTVAASPKARDRGALIVMNDRIVSAFYASKTNANTVDTFKAIEMGNLGEVVS
SEQ ID NO: 3       GPFNLLQAVTVAAHPTARNRGALVVMNDRIVSAYYVSKTNANTMDTFKAVEMGNLGAIIS
SEQ ID NO: 6       GPFNLLQSVTVAATPAARDRGALVVLNDRVLSAFYTSKTNANTMDTFKAIEMGALAAIVS

SEQ ID NO: 5       NKPYFYYPAVEPNAKHVVHLDDVDAIPRVDILYAYEDMHSDLHSAIKNGAKGIVVAGEG
SEQ ID NO: 2       NTPFFFYPPVKPTGKVAFDITNVTEIPRVDILFSYEDMHNDTLYNAISSGAQGIVIAGAG
SEQ ID NO: 4       NTPFFYYPAVQPSGKTTVDVSNVTSIPRVDILYSFQDMTNDTLYSSIENGAKGVVIAGSG
SEQ ID NO: 1       NKPYFYYPPVKPTGKTEVDIRNITSIPRVDILYSYEDMHNDTLYSAIDNGAKGIVIAGSG
SEQ ID NO: 3       NKPYFYYPPVMPTGKTTFDVRNVASIPRVDILYSYQDMQNDTLYDAVDNGAKGIVIAGSG
SEQ ID NO: 6       NKPYFYYPPVRPTGHEFFDVRNVSALPRVDILYSYQDMQNDTLYDAAKNGAKGIVIAGSG

SEQ ID NO: 5       AGGISTDFSDTIDEIASKHQIPIILSHRTVNGEVPTADITGDSAKTRIASGMYNPQQARV
SEQ ID NO: 2       AGGVTTSFNEAIEDVINRLEIPVVQSMRTVNGEVPLSDVSSDTA-THIASGYLNPQKSRI
SEQ ID NO: 4       AGSVDTAFSTAIDDIISNQGVPIVQSTRTGNGEVPYSA-E-----GGISSGFLNPAKSRI
SEQ ID NO: 1       SGSVSTPFSAAMEDITTKHNIPIVASTRTGNGEVPSSAES-----SQIASGYLNPAKSRV
SEQ ID NO: 3       AGSVSSGYYDAIDDIASTHSLPVVLSTRTGNGEVAITDSE-----TTIESGFLNPQKARI
SEQ ID NO: 6       AGSVSSGFSAAIEDVMDTYHIPVVASTRTGNGEVPPSD-D-----GAIGSGFLNPQKSRI

SEQ ID NO: 5       LLGLLLAE-GKKFEDIRTIFGKATVA
SEQ ID NO: 2       LLGLLLSQ-GKNITEIADVFALGTDA
SEQ ID NO: 4       LLGLLLAQGGKGTEEIRAVFGKVAV-
SEQ ID NO: 1       LLGLLLAQ-GKSIEEMRAVFERIGVA
SEQ ID NO: 3       LLGLLLAE-DKGFKEIKEAFAKNGVA
SEQ ID NO: 6       WLELLLMQ-KKTVAEVREMFAKVAVA
```

Figure 1

Parameter file for Molecular Dynamics Simulation em.mdp

```
; VARIOUS PREPROCESSING OPTIONS =
title                        =
cpp                          = /lib/cpp
include                      =
define                       = -DFLEXIBLE ; RUN CONTROL PARAMETERS =
integrator                   = steep
; start time and timestep in ps =
tinit                        = 0
dt                           = 0.001
nsteps                       = 100

; ENERGY MINIMIZATION OPTIONS =
emtol                        = 0.00001
emstep                       = 0.1
nstcgsteep                   = 1000
```

Figure 2

Parameter file for Molecular Dynamics Simulation md.mdp

```
title          = asparaginase
cpp            = /lib/cpp
constraints    = all-bonds
integrator     = md
dt             = 0.002      ; ps !
nsteps         = 5000       ; total 5 ps.
nstcomm        = 1
nstxout        = 50
nstvout        = 0
nstfout        = 0
nstlist        = 10
ns_type        = grid
rlist          = 1.0
rcoulomb       = 1.0
rvdw           = 1.0
; Berendsen temperature coupling is on in two groups
Tcoupl         = berendsen
tau_t          = 0.1        0.1
tc-grps        = protein    sol
ref_t          = 300        300
; Pressure coupling is not on
Pcoupl         = no
tau_p          = 0.5
compressibility = 4.5e-5
ref_p          = 1.0
; Generate velocites is on at 300 K.
gen_vel        = yes
gen_temp       = 300.0
gen_seed       = 173529
```

Figure 3

SEQUENCE LISTING

<160> NUMBER OF SEQ ID NOS: 15

<210> SEQ ID NO 1
<211> LENGTH: 378
<212> TYPE: PRT
<213> ORGANISM: Aspergillus oryzae

<400> SEQUENCE: 1

Met Gly Val Asn Phe Lys Val Leu Ala Leu Ser Ala Leu Ala Thr Ile

```
1               5                   10                  15

Ser His Ala Ser Pro Leu Leu Tyr Pro Arg Ala Thr Asp Ser Asn Val
                    20                  25                  30

Thr Tyr Val Phe Thr Asn Pro Asn Gly Leu Asn Phe Thr Gln Met Asn
                    35                  40                  45

Thr Thr Leu Pro Asn Val Thr Ile Phe Ala Thr Gly Gly Thr Ile Ala
 50                      55                  60

Gly Ser Ser Ala Asp Asn Thr Ala Thr Thr Gly Tyr Lys Ala Gly Ala
 65                      70                  75                  80

Val Gly Ile Gln Thr Leu Ile Asp Ala Val Pro Glu Met Leu Asn Val
                    85                  90                  95

Ala Asn Val Ala Gly Val Gln Val Thr Asn Val Gly Ser Pro Asp Ile
                    100                 105                 110

Thr Ser Asp Ile Leu Leu Arg Leu Ser Lys Gln Ile Asn Glu Val Val
                    115                 120                 125

Cys Asn Asp Pro Thr Met Ala Gly Ala Val Val Thr His Gly Thr Asp
                    130                 135                 140

Thr Leu Glu Glu Ser Ala Phe Phe Leu Asp Ala Thr Val Asn Cys Arg
145                     150                 155                 160

Lys Pro Val Val Ile Val Gly Ala Met Arg Pro Ser Thr Ala Ile Ser
                    165                 170                 175

Ala Asp Gly Pro Leu Asn Leu Leu Gln Ser Val Thr Val Ala Ala Ser
                    180                 185                 190

Pro Lys Ala Arg Asp Arg Gly Ala Leu Ile Val Met Asn Asp Arg Ile
                    195                 200                 205

Val Ser Ala Phe Tyr Ala Ser Lys Thr Asn Ala Asn Thr Val Asp Thr
                    210                 215                 220

Phe Lys Ala Ile Glu Met Gly Asn Leu Gly Glu Val Val Ser Asn Lys
225                     230                 235                 240

Pro Tyr Phe Phe Tyr Pro Pro Val Lys Pro Thr Gly Lys Thr Glu Val
                    245                 250                 255

Asp Ile Arg Asn Ile Thr Ser Ile Pro Arg Val Asp Ile Leu Tyr Ser
                    260                 265                 270

Tyr Glu Asp Met His Asn Asp Thr Leu Tyr Ser Ala Ile Asp Asn Gly
                    275                 280                 285

Ala Lys Gly Ile Val Ile Ala Gly Ser Gly Ser Gly Ser Val Ser Thr
                    290                 295                 300

Pro Phe Ser Ala Ala Met Glu Asp Ile Thr Thr Lys His Asn Ile Pro
305                     310                 315                 320

Ile Val Ala Ser Thr Arg Thr Gly Asn Gly Glu Val Pro Ser Ser Ala
                    325                 330                 335

Glu Ser Ser Gln Ile Ala Ser Gly Tyr Leu Asn Pro Ala Lys Ser Arg
                    340                 345                 350

Val Leu Leu Gly Leu Leu Ala Gln Gly Lys Ser Ile Glu Glu Met
                    355                 360                 365

Arg Ala Val Phe Glu Arg Ile Gly Val Ala
370                     375

<210> SEQ ID NO 2
<211> LENGTH: 378
<212> TYPE: PRT
<213> ORGANISM: Aspergillus niger

<400> SEQUENCE: 2
```

```
Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
            20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
                100                 105                 110

Leu Ile Ser Met Ser Lys Lys Leu Asn Arg Val Val Cys Glu Asp Pro
            115                 120                 125

Thr Met Ala Gly Ala Val Ile Thr His Gly Thr Asp Thr Leu Glu Glu
        130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
210                 215                 220

Glu Met Gly Tyr Leu Gly Glu Met Ile Ser Asn Thr Pro Phe Phe Phe
225                 230                 235                 240

Tyr Pro Pro Val Lys Pro Thr Gly Lys Val Ala Phe Asp Ile Thr Asn
                245                 250                 255

Val Thr Glu Ile Pro Arg Val Asp Ile Leu Phe Ser Tyr Glu Asp Met
            260                 265                 270

His Asn Asp Thr Leu Tyr Asn Ala Ile Ser Ser Gly Ala Gln Gly Ile
        275                 280                 285

Val Ile Ala Gly Ala Gly Ala Gly Gly Val Thr Thr Ser Phe Asn Glu
290                 295                 300

Ala Ile Glu Asp Val Ile Asn Arg Leu Glu Ile Pro Val Val Gln Ser
305                 310                 315                 320

Met Arg Thr Val Asn Gly Glu Val Pro Leu Ser Asp Val Ser Ser Asp
                325                 330                 335

Thr Ala Thr His Ile Ala Ser Gly Tyr Leu Asn Pro Gln Lys Ser Arg
            340                 345                 350

Ile Leu Leu Gly Leu Leu Leu Ser Gln Gly Lys Asn Ile Thr Glu Ile
        355                 360                 365

Ala Asp Val Phe Ala Leu Gly Thr Asp Ala
    370                 375

<210> SEQ ID NO 3
<211> LENGTH: 374
<212> TYPE: PRT
<213> ORGANISM: Aspergillus fumigatus

<400> SEQUENCE: 3
```

```
Met Thr Lys Leu Ser Phe Lys Ile Ile Thr Leu Ala Ala Met Ile Ala
1               5                   10                  15

Val Gly Asn Ala Ser Pro Phe Val Tyr Pro Arg Ala Thr Ser Pro Asn
            20                  25                  30

Ser Thr Tyr Val Phe Thr Asn Ser His Gly Leu Asn Phe Thr Gln Met
                35                  40                  45

Asn Thr Thr Leu Pro Asn Val Thr Ile Leu Ala Thr Gly Gly Thr Ile
50                  55                  60

Ala Gly Ser Ser Asn Asp Asn Thr Ala Thr Thr Gly Tyr Thr Ala Gly
65                  70                  75                  80

Ala Ile Gly Ile Gln Gln Leu Met Asp Ala Val Pro Glu Met Leu Asp
                85                  90                  95

Val Ala Asn Val Ala Gly Ile Gln Val Ala Asn Val Gly Ser Pro Asp
                100                 105                 110

Val Thr Ser Ser Leu Leu Leu His Met Ala Arg Thr Ile Asn Glu Val
                115                 120                 125

Val Cys Asp Asp Pro Thr Met Ser Gly Ala Val Ile Thr His Gly Thr
130                 135                 140

Asp Thr Leu Glu Glu Thr Ala Phe Phe Leu Asp Ala Thr Val Asn Cys
145                 150                 155                 160

Gly Lys Pro Ile Val Val Gly Ala Met Arg Pro Ala Thr Ala Ile
                165                 170                 175

Ser Ala Asp Gly Pro Phe Asn Leu Leu Gln Ala Val Thr Val Ala Ala
                180                 185                 190

His Pro Thr Ala Arg Asn Arg Gly Ala Leu Val Val Met Asn Asp Arg
        195                 200                 205

Ile Val Ser Ala Tyr Tyr Val Ser Lys Thr Asn Ala Asn Thr Met Asp
        210                 215                 220

Thr Phe Lys Ala Val Glu Met Gly Asn Leu Gly Ala Ile Ile Ser Asn
225                 230                 235                 240

Lys Pro Tyr Phe Phe Tyr Pro Pro Val Met Pro Thr Gly Lys Thr Thr
                245                 250                 255

Phe Asp Val Arg Asn Val Ala Ser Ile Pro Arg Val Asp Ile Leu Tyr
                260                 265                 270

Ser Tyr Gln Asp Met Gln Asn Asp Thr Leu Tyr Asp Ala Val Asp Asn
                275                 280                 285

Gly Ala Lys Gly Ile Val Arg Ser Val Ser Ser Gly Tyr Tyr Asp
        290                 295                 300

Ala Ile Asp Asp Ile Ala Ser Thr His Ser Leu Pro Val Val Leu Ser
305                 310                 315                 320

Thr Arg Thr Gly Asn Gly Glu Val Ala Ile Thr Asp Ser Glu Thr Thr
                325                 330                 335

Ile Glu Ser Gly Phe Leu Asn Pro Gln Lys Ala Arg Ile Leu Leu Gly
            340                 345                 350

Leu Leu Leu Ala Glu Asp Lys Gly Phe Lys Glu Ile Lys Glu Ala Phe
            355                 360                 365

Ala Lys Asn Gly Val Ala
        370

<210> SEQ ID NO 4
<211> LENGTH: 378
<212> TYPE: PRT
<213> ORGANISM: Aspergillus nidulans
```

<400> SEQUENCE: 4

```
Met Gly Leu Arg Val Lys Ala Leu Ala Val Ala Ala Leu Ala Thr Leu
 1               5                  10                  15

Ser Gln Ala Ser Pro Val Leu Tyr Thr Arg Glu Asp Thr Thr Ser Asn
            20                  25                  30

Thr Thr Tyr Ala Phe Thr Asn Ser Asn Gly Leu Asn Phe Thr Gln Met
        35                  40                  45

Asn Thr Thr Leu Pro Asn Val Thr Ile Phe Ala Thr Gly Gly Thr Ile
50                  55                  60

Ala Gly Ser Ala Ala Ser Asn Thr Ala Thr Thr Gly Tyr Gln Ala Gly
65                  70                  75                  80

Ala Leu Gly Ile Gln Thr Leu Ile Asp Ala Val Pro Glu Met Leu Ser
                85                  90                  95

Val Ala Asn Ile Ala Gly Val Gln Ile Ser Asn Val Gly Ser Pro Asp
            100                 105                 110

Val Thr Ser Thr Ile Leu Leu Glu Met Ala His Arg Leu Asn Lys Val
        115                 120                 125

Val Cys Glu Asp Pro Ser Met Ala Gly Ala Val Val Thr His Gly Thr
130                 135                 140

Asp Thr Leu Glu Glu Thr Ala Phe Phe Leu Asp Ala Thr Val Asn Cys
145                 150                 155                 160

Gly Lys Pro Ile Val Ile Val Gly Ala Met Arg Pro Ala Thr Phe Ile
                165                 170                 175

Ser Ala Asp Gly Pro Tyr Asn Leu Leu Gln Ala Val Thr Val Ala Ser
            180                 185                 190

Thr Lys Glu Ala Arg Asn Arg Gly Ala Met Val Val Met Asn Asp Arg
        195                 200                 205

Ile Ala Ser Ala Tyr Tyr Val Ser Lys Thr Asn Ala Asn Thr Met Asp
210                 215                 220

Thr Phe Lys Ala Val Glu Met Gly Tyr Leu Gly Ala Ile Ile Ser Asn
225                 230                 235                 240

Thr Pro Phe Phe Tyr Tyr Pro Ala Val Gln Pro Ser Gly Lys Thr Thr
                245                 250                 255

Val Asp Val Ser Asn Val Thr Ser Ile Pro Arg Val Asp Ile Leu Tyr
            260                 265                 270

Ser Phe Gln Asp Met Thr Asn Asp Thr Leu Tyr Ser Ser Ile Glu Asn
        275                 280                 285

Gly Ala Lys Gly Val Val Ile Ala Gly Ser Gly Ala Gly Ser Val Asp
290                 295                 300

Thr Ala Phe Ser Thr Ala Ile Asp Asp Ile Ile Ser Asn Gln Gly Val
305                 310                 315                 320

Pro Ile Val Gln Ser Thr Arg Thr Gly Asn Gly Glu Val Pro Tyr Ser
                325                 330                 335

Ala Glu Gly Gly Ile Ser Ser Gly Phe Leu Asn Pro Ala Lys Ser Arg
            340                 345                 350

Ile Leu Leu Gly Leu Leu Leu Ala Gln Gly Gly Lys Gly Thr Glu Glu
        355                 360                 365

Ile Arg Ala Val Phe Gly Lys Val Ala Val
370                 375
```

<210> SEQ ID NO 5
<211> LENGTH: 379
<212> TYPE: PRT
<213> ORGANISM: Penicillium citrinum

```
<220> FEATURE:
<221> NAME/KEY: misc_feature
<222> LOCATION: (110)..(110)
<223> OTHER INFORMATION: Xaa can be any naturally occurring amino acid

<400> SEQUENCE: 5

Met Arg Leu Leu Phe Asn Thr Leu Ala Val Ser Ala Leu Ala Ala Thr
1               5                   10                  15

Ser Tyr Ala Ser Pro Ile Ile His Ser Arg Ala Ser Asn Thr Ser Tyr
            20                  25                  30

Thr Asn Ser Asn Gly Leu Lys Phe Asn His Phe Asp Ala Ser Leu Pro
        35                  40                  45

Asn Val Thr Leu Leu Ala Thr Gly Gly Thr Ile Ala Gly Thr Ser Asp
    50                  55                  60

Asp Lys Thr Ala Thr Ala Gly Tyr Glu Ser Gly Ala Leu Gly Ile Asn
65                  70                  75                  80

Lys Ile Leu Ser Gly Ile Pro Glu Val Tyr Asp Ile Ala Asn Val Asn
                85                  90                  95

Ala Val Gln Phe Asp Asn Val Asn Ser Gly Asp Val Ser Xaa Ser Leu
            100                 105                 110

Leu Leu Asn Met Thr His Thr Leu Gln Lys Thr Val Cys Asp Asp Pro
        115                 120                 125

Thr Ile Ser Gly Ala Val Ile Thr His Gly Thr Asp Thr Leu Glu Glu
    130                 135                 140

Ser Ala Phe Phe Ile Asp Ala Thr Val Asn Cys Gly Lys Pro Ile Val
145                 150                 155                 160

Phe Val Gly Ser Met Arg Pro Ser Thr Ala Ile Ser Ala Asp Gly Pro
                165                 170                 175

Met Asn Leu Leu Gln Gly Val Thr Val Ala Ala Asp Lys Gln Ala Lys
            180                 185                 190

Asn Arg Gly Ala Leu Val Val Leu Asn Asp Arg Ile Val Ser Ala Phe
        195                 200                 205

Phe Ala Thr Lys Thr Asn Ala Asn Thr Met Asp Thr Phe Lys Ala Tyr
    210                 215                 220

Glu Gln Gly Ser Leu Gly Met Ile Val Ser Asn Lys Pro Tyr Phe Tyr
225                 230                 235                 240

Tyr Pro Ala Val Glu Pro Asn Ala Lys His Val Val His Leu Asp Asp
                245                 250                 255

Val Asp Ala Ile Pro Arg Val Asp Ile Leu Tyr Ala Tyr Glu Asp Met
            260                 265                 270

His Ser Asp Ser Leu His Ser Ala Ile Lys Asn Gly Ala Lys Gly Ile
        275                 280                 285

Val Val Ala Gly Glu Gly Ala Gly Gly Ile Ser Thr Asp Phe Ser Asp
    290                 295                 300

Thr Ile Asp Glu Ile Ala Ser Lys His Gln Ile Pro Ile Ile Leu Ser
305                 310                 315                 320

His Arg Thr Val Asn Gly Glu Val Pro Thr Ala Asp Ile Thr Gly Asp
                325                 330                 335

Ser Ala Lys Thr Arg Ile Ala Ser Gly Met Tyr Asn Pro Gln Gln Ala
            340                 345                 350

Arg Val Leu Leu Gly Leu Leu Leu Ala Glu Gly Lys Lys Phe Glu Asp
        355                 360                 365

Ile Arg Thr Ile Phe Gly Lys Ala Thr Val Ala
    370                 375
```

<210> SEQ ID NO 6
<211> LENGTH: 375
<212> TYPE: PRT
<213> ORGANISM: Aspergillus terreus

<400> SEQUENCE: 6

```
Met Gly Phe Asn Ile Lys Ala Leu Thr Val Ala Ala Leu Ala Ala Leu
1               5                   10                  15

Gly His Ala Ser Pro Leu Tyr Ser Arg Ala Asp Ala Asn Val Thr Tyr
            20                  25                  30

Val Phe Thr Asn Ala His Gly Leu Asn Phe Thr Gln Met Asn Thr Thr
        35                  40                  45

Leu Pro Asn Val Thr Ile Leu Ala Thr Gly Gly Thr Ile Ala Gly Ser
    50                  55                  60

Ser Ala Asp Asn Thr Ala Thr Thr Gly Tyr Lys Ala Gly Ala Ile Gly
65                  70                  75                  80

Ile Gln Gln Leu Ile Asp Ala Val Pro Glu Met Leu Asn Val Ala Asn
                85                  90                  95

Val Ala Gly Val Gln Val Thr Asn Val Gly Ser Pro Asp Val Thr Ser
            100                 105                 110

His Ile Leu Leu Asp Met Val Arg Met Leu Asp Glu Leu Val Cys Gln
        115                 120                 125

Asp Glu Thr Met Ala Gly Ala Val Ile Thr His Gly Thr Asp Thr Leu
    130                 135                 140

Glu Glu Thr Ala Phe Phe Leu Asp Ala Thr Met Pro Cys Arg Lys Pro
145                 150                 155                 160

Val Val Val Val Gly Ala Met Arg Pro Ser Thr Ala Ile Ser Ala Asp
                165                 170                 175

Gly Pro Phe Asn Leu Leu Gln Ser Val Thr Val Ala Ala Thr Pro Ala
            180                 185                 190

Ala Arg Asp Arg Gly Ala Leu Val Val Leu Asn Asp Arg Val Leu Ser
        195                 200                 205

Ala Phe Tyr Thr Ser Lys Thr Asn Ala Asn Thr Met Asp Thr Phe Lys
    210                 215                 220

Ala Ile Glu Met Gly Ala Leu Ala Ala Ile Val Ser Asn Lys Pro Tyr
225                 230                 235                 240

Phe Tyr Tyr Pro Pro Val Arg Pro Thr Gly His Glu Phe Phe Asp Val
                245                 250                 255

Arg Asn Val Ser Ala Leu Pro Arg Val Asp Ile Leu Tyr Ser Tyr Gln
            260                 265                 270

Asp Met Gln Asn Asp Thr Leu Tyr Asp Ala Ala Lys Asn Gly Ala Lys
        275                 280                 285

Gly Ile Val Ile Ala Gly Ser Gly Ala Gly Ser Val Ser Ser Gly Phe
    290                 295                 300

Ser Ala Ala Ile Glu Asp Val Met Asp Thr Tyr His Ile Pro Val Val
305                 310                 315                 320

Ala Ser Thr Arg Thr Gly Asn Gly Glu Val Pro Pro Ser Asp Asp Gly
                325                 330                 335

Ala Ile Gly Ser Gly Phe Leu Asn Pro Gln Lys Ser Arg Ile Trp Leu
            340                 345                 350

Glu Leu Leu Leu Met Gln Lys Lys Thr Val Ala Glu Val Arg Glu Met
        355                 360                 365

Phe Ala Lys Val Ala Val Ala
    370                 375
```

<210> SEQ ID NO 7
<211> LENGTH: 41
<212> TYPE: DNA
<213> ORGANISM: Artificial sequence
<220> FEATURE:
<223> OTHER INFORMATION: primer

<400> SEQUENCE: 7
agccttgttg ctgctctccc cgccacagac tcgaacgtca c                           41

<210> SEQ ID NO 8
<211> LENGTH: 50
<212> TYPE: DNA
<213> ORGANISM: Artificial sequence
<220> FEATURE:
<223> OTHER INFORMATION: primer

<400> SEQUENCE: 8
agtcaccctc tagatctcga cttaattaat caagcaaccc caatccgctc                  50

<210> SEQ ID NO 9
<211> LENGTH: 255
<212> TYPE: PRT
<213> ORGANISM: Artificial sequence
<220> FEATURE:
<223> OTHER INFORMATION: Synthetic construct

<400> SEQUENCE: 9

Pro Asn Ile Val Ile Leu Ala Thr Gly Gly Thr Ile Ala Gly Ala Ala
1               5                   10                  15

Ala Ser Ala Thr Val Asp Thr Leu Ile Glu Ala Val Pro Glu Leu Lys
            20                  25                  30

Asp Leu Ala Asn Val Lys Gly Glu Gln Val Ala Asn Ile Gly Ser Glu
        35                  40                  45

Asp Met Asn Asn Glu Ile Leu Leu Lys Leu Gly Ile Val Ile Thr His
    50                  55                  60

Gly Thr Asp Thr Leu Glu Glu Thr Ala Tyr Phe Leu Asn Leu Thr Val
65                  70                  75                  80

Lys Ser Asp Lys Pro Val Val Leu Val Gly Ala Met Arg Pro Ala Thr
                85                  90                  95

Ala Ile Ser Ala Asp Gly Pro Met Asn Leu Tyr Asn Ala Val Ala Val
            100                 105                 110

Ala Ala Asp Lys Glu Ala Arg Gly Lys Gly Val Leu Val Val Met Asn
        115                 120                 125

Asp Arg Ile Gly Ser Ala Arg Tyr Val Thr Lys Thr Asn Thr Thr Thr
    130                 135                 140

Val Asp Ala Phe Lys Ala Pro Gly Tyr Leu Gly Val Ile Val Asn Gly
145                 150                 155                 160

Lys Val Tyr Phe Phe Thr Arg Pro His Thr Thr Asn Ser Glu Phe Asp
                165                 170                 175

Val Arg Lys Ile Asp Ser Leu Pro Lys Val Asp Ile Leu Tyr Ser Tyr
            180                 185                 190

Gln Asn Ala Ala Ile Asp Asn Gly Ala Lys Gly Ile Val Tyr Ala Gly
        195                 200                 205

Thr Gly Asn Gly Ser Val Ser Lys Arg Ala Lys Ala Gly Leu Lys Lys
    210                 215                 220

Ala Gly Ile Val Val Arg Ser Ser Arg Val Gly Asn Gly Leu Asn
225                 230                 235                 240

```
Pro Gln Lys Ala Arg Ile Leu Leu Met Leu Ala Leu Thr Gln Thr
                245                 250                 255

<210> SEQ ID NO 10
<211> LENGTH: 255
<212> TYPE: PRT
<213> ORGANISM: Artificial sequence
<220> FEATURE:
<223> OTHER INFORMATION: Synthetic construct

<400> SEQUENCE: 10

Pro Asn Ile Val Ile Leu Ala Thr Gly Gly Thr Ile Ala Gly Ala Gly
1               5                   10                  15

Ala Ser Ala Thr Val Asp Thr Leu Ile Glu Ala Val Pro Glu Leu Lys
            20                  25                  30

Asp Leu Ala Asn Val Lys Gly Glu Gln Val Ala Asn Ile Gly Ser Glu
        35                  40                  45

Asp Met Asn Asn Glu Ile Leu Lys Leu Gly Ile Val Ile Thr His
    50                  55                  60

Gly Thr Asp Thr Leu Glu Glu Thr Ala Tyr Phe Leu Asn Leu Thr Val
65                  70                  75                  80

Lys Ser Asp Lys Pro Val Val Leu Val Gly Ala Met Arg Pro Ala Thr
                85                  90                  95

Ala Ile Ser Ala Asp Gly Pro Met Asn Leu Tyr Asn Ala Val Ala Val
            100                 105                 110

Ala Ala Asp Lys Glu Ser Arg Gly Lys Gly Val Leu Val Val Met Asn
        115                 120                 125

Asp Arg Ile Gln Ser Ala Arg Tyr Val Thr Lys Thr Asn Thr Thr Asn
    130                 135                 140

Val Asp Ala Phe Lys Ser Pro Gly Pro Leu Gly Tyr Ile Val Asn Gly
145                 150                 155                 160

Lys Val Tyr Phe Phe Arg Ser Pro His Thr Thr Asn Ser Glu Phe Asp
                165                 170                 175

Val Arg Lys Ile Asp Ser Leu Pro Lys Val Asp Ile Leu Tyr Ser Tyr
            180                 185                 190

Ala Asn Ala Leu Ile Asp Asn Gly Ala Lys Gly Ile Val His Ala Gly
        195                 200                 205

Thr Gly Asn Gly Ser Ile Ser Lys Arg Leu Lys Asp Ala Leu Lys Lys
    210                 215                 220

Ala Gly Ile Val Val Arg Ser Ser Arg Val Gly Gln Gly Leu Asn
225                 230                 235                 240

Pro Gln Lys Ala Arg Ile Leu Leu Met Leu Ala Leu Thr Gln Thr
                245                 250                 255

<210> SEQ ID NO 11
<211> LENGTH: 333
<212> TYPE: PRT
<213> ORGANISM: Artificial sequence
<220> FEATURE:
<223> OTHER INFORMATION: Synthetic construct

<400> SEQUENCE: 11

Met Leu Ala Leu Leu Ser Ala Ala Pro Ala Leu Pro Asn Ile Thr Ile
1               5                   10                  15

Leu Ala Thr Gly Gly Thr Ile Ala Gly Ala Ala Ser Ala Thr Gln
            20                  25                  30

Thr Thr Gly Tyr Thr Ala Gly Ala Val Gly Val Asp Thr Leu Ile Ala
```

```
                35                  40                  45
Ala Val Pro Glu Leu Lys Asp Leu Ala Asn Val Ala Gly Glu Gln Val
        50                  55                  60
Ala Asn Ile Asp Ser Glu Asp Ile Thr Asn Ala Ile Leu Leu Lys Leu
65                  70                  75                  80
Ala Lys Arg Val Asn Ala Leu Leu Ala Asp Pro Asp Val Asp Gly Ile
                85                  90                  95
Val Ile Thr His Gly Thr Asp Thr Leu Glu Glu Thr Ala Tyr Phe Leu
            100                 105                 110
Asn Leu Thr Leu Lys Ser Ala Lys Pro Val Val Leu Val Gly Ala Met
            115                 120                 125
Arg Pro Ala Thr Ala Leu Ser Ala Asp Gly Pro Leu Asn Leu Tyr Asn
        130                 135                 140
Ala Val Ala Val Ala Ala Asp Lys Ala Ala Arg Gly Lys Gly Val Leu
145                 150                 155                 160
Val Ala Met Asn Asp Arg Ile Gly Ser Ala Arg Phe Val Thr Lys Ala
                165                 170                 175
Asn Thr Thr Asp Leu Asp Ala Phe Lys Ala Pro Glu Gln Gly Asn Leu
            180                 185                 190
Gly Ala Ile Ala Asn Gly Lys Val Tyr Phe Phe Thr Ser Pro Ala Lys
            195                 200                 205
Arg His Thr Leu Asp Ser Glu Phe Asp Arg Ala Ile Asp Ser Leu Pro
        210                 215                 220
Lys Val Asp Ile Leu Tyr Asp Tyr Gln Asp Ala Asp Ala Asp Ala Tyr
225                 230                 235                 240
Asp Ala Ala Ile Asp Asn Gly Ala Lys Gly Ile Val Ile Ala Gly Ser
                245                 250                 255
Gly Asn Gly Ser Val Ser Lys Arg Ala Lys Ala Ala Lys Lys Ala
            260                 265                 270
Ala Lys Glu Gly Ile Ile Val Val Arg Ser Ser Arg Val Gly Asn Gly
            275                 280                 285
Val Val Leu Asp Ala Ala Asp Asp Ala Gly Val Ala Ala Gly Ser Leu
        290                 295                 300
Asn Pro Gln Lys Ala Arg Ile Leu Leu Met Leu Ala Leu Thr Lys Thr
305                 310                 315                 320
Lys Asp Pro Glu Glu Ile Gln Arg Tyr Phe Asp Gln Tyr
                325                 330

<210> SEQ ID NO 12
<211> LENGTH: 332
<212> TYPE: PRT
<213> ORGANISM: Artificial sequence
<220> FEATURE:
<223> OTHER INFORMATION: Synthetic construct

<400> SEQUENCE: 12

Met Leu Leu Leu Ala Ala Pro Ala Leu Pro Asn Ile Thr Ile Leu Ala
1               5                   10                  15
Thr Gly Gly Thr Ile Ala Gly Ala Gly Ala Ser Ala Thr Asp Thr Thr
                20                  25                  30
Gly Tyr Thr Ala Gly Lys Val Gly Val Asp Thr Leu Ile Ala Ala Val
            35                  40                  45
Pro Glu Leu Lys Asp Leu Ala Asn Val Ala Gly Glu Gln Val Ala Asn
        50                  55                  60
Ile Asp Ser Glu Asp Ile Thr Asn Glu Ile Leu Leu Lys Leu Ala Lys
```

```
                65                  70                  75                  80
Arg Val Asn Ala Leu Leu Asp Asp Pro Asp Val Asp Gly Ile Val Ile
                        85                  90                  95
Thr His Gly Thr Asp Thr Leu Glu Glu Thr Ala Tyr Phe Leu Asn Leu
                        100                 105                 110
Thr Leu Lys Ser Asp Lys Pro Val Val Leu Val Gly Ala Met Arg Pro
                        115                 120                 125
Ala Thr Ala Leu Ser Ala Asp Gly Pro Leu Asn Leu Tyr Asn Ala Val
                        130                 135                 140
Ala Val Ala Ala Asp Lys Ala Arg Gly Lys Gly Val Leu Val Ala
145                     150                 155                 160
Met Asn Asp Arg Ile Gly Ser Ala Arg Asp Val Ala Lys Ala Asn Thr
                        165                 170                 175
Thr Asp Leu Asp Ala Phe Lys Ser Pro Phe Gly Pro Leu Gly Ala Ile
                        180                 185                 190
Ala Asn Gly Lys Val Tyr Phe Phe Arg Ser Pro Ala Lys Arg His Thr
                        195                 200                 205
Leu Asp Ser Glu Phe Asp Val Arg Ala Ile Asp Ser Leu Pro Lys Val
                        210                 215                 220
Asp Ile Leu Tyr Ser Tyr Ala Asn Ala Asp Ala Asp Ala Tyr Lys Ala
225                     230                 235                 240
Leu Ala Asp Asn Gly Ala Lys Gly Ile Val His Ala Gly Ser Gly Asn
                        245                 250                 255
Gly Ser Val Ser Lys Arg Ala Lys Ala Ala Leu Lys Lys Ala Ala Lys
                        260                 265                 270
Glu Gly Ile Ile Val Val Arg Ser Ser Arg Val Asn Asn Gly Val Leu
                        275                 280                 285
Asp Ala Ala Asp Asp Ala Lys Leu Gly Val Ala Ala Gly Asp Leu Asn
                        290                 295                 300
Pro Gln Lys Ala Arg Ile Leu Leu Met Leu Ala Leu Thr Lys Thr Lys
305                     310                 315                 320
Asp Pro Lys Glu Ile Gln Arg Tyr Phe Asp Glu Tyr
                        325                 330

<210> SEQ ID NO 13
<211> LENGTH: 329
<212> TYPE: PRT
<213> ORGANISM: Aspergillus oryzae

<400> SEQUENCE: 13

Thr Leu Pro Asn Val Thr Ile Phe Ala Thr Gly Gly Thr Ile Ala Gly
1               5                   10                  15
Ser Ser Ala Asp Asn Thr Ala Thr Thr Gly Tyr Lys Ala Gly Ala Val
                20                  25                  30
Gly Ile Gln Thr Leu Ile Asp Ala Val Pro Glu Met Leu Asn Val Ala
                35                  40                  45
Asn Val Ala Gly Val Gln Val Thr Asn Val Gly Ser Pro Asp Ile Thr
                50                  55                  60
Ser Asp Ile Leu Leu Arg Leu Ser Lys Gln Ile Asn Glu Val Val Cys
65                      70                  75                  80
Asn Asp Pro Thr Met Ala Gly Ala Val Val Thr His Gly Thr Asp Thr
                        85                  90                  95
Leu Glu Glu Ser Ala Phe Phe Leu Asp Ala Thr Val Asn Cys Arg Lys
                        100                 105                 110
```

```
Pro Val Val Ile Val Gly Ala Met Arg Pro Ser Thr Ala Ile Ser Ala
            115                 120                 125

Asp Gly Pro Leu Asn Leu Leu Gln Ser Val Thr Val Ala Ala Ser Pro
130                 135                 140

Lys Ala Arg Asp Arg Gly Ala Leu Ile Val Met Asn Asp Arg Ile Val
145                 150                 155                 160

Ser Ala Phe Tyr Ala Ser Lys Thr Asn Ala Asn Thr Val Asp Thr Phe
                165                 170                 175

Lys Ala Ile Glu Met Gly Asn Leu Gly Glu Val Val Ser Asn Lys Pro
            180                 185                 190

Tyr Phe Phe Tyr Pro Pro Val Lys Pro Thr Gly Lys Thr Glu Val Asp
        195                 200                 205

Ile Arg Asn Ile Thr Ser Ile Pro Arg Val Asp Ile Leu Tyr Ser Tyr
    210                 215                 220

Glu Asp Met His Asn Asp Thr Leu Tyr Ser Ala Ile Asp Asn Gly Ala
225                 230                 235                 240

Lys Gly Ile Val Ile Ala Gly Ser Gly Ser Val Ser Thr Pro
                245                 250                 255

Phe Ser Ala Ala Met Glu Asp Ile Thr Thr Lys His Asn Ile Pro Ile
            260                 265                 270

Val Ala Ser Thr Arg Thr Gly Asn Gly Glu Val Pro Ser Ser Ala Glu
        275                 280                 285

Ser Ser Gln Ile Ala Ser Gly Tyr Leu Asn Pro Ala Lys Ser Arg Val
    290                 295                 300

Leu Leu Gly Leu Leu Leu Ala Gln Gly Lys Ser Ile Glu Glu Met Arg
305                 310                 315                 320

Ala Val Phe Glu Arg Ile Gly Val Ala
                325

<210> SEQ ID NO 14
<211> LENGTH: 325
<212> TYPE: PRT
<213> ORGANISM: Erwinia chrysanthemi

<400> SEQUENCE: 14

Lys Leu Pro Asn Ile Val Ile Leu Ala Thr Gly Gly Thr Ile Ala Gly
1               5                   10                  15

Ser Ala Ala Thr Gly Thr Gln Thr Thr Gly Tyr Lys Ala Gly Ala Leu
            20                  25                  30

Gly Val Asp Thr Leu Ile Asn Ala Val Pro Glu Val Lys Lys Leu Ala
        35                  40                  45

Asn Val Lys Gly Glu Gln Phe Ser Asn Met Ala Ser Glu Asn Met Thr
    50                  55                  60

Gly Asp Val Val Leu Lys Leu Ser Gln Arg Val Asn Glu Leu Leu Ala
65                  70                  75                  80

Arg Asp Asp Val Asp Gly Val Val Ile Thr His Gly Thr Asp Thr Val
                85                  90                  95

Glu Glu Ser Ala Tyr Phe Leu His Leu Thr Val Lys Ser Asp Lys Pro
            100                 105                 110

Val Val Phe Val Ala Ala Met Arg Pro Ala Thr Ala Ile Ser Ala Asp
        115                 120                 125

Gly Pro Met Asn Leu Leu Glu Ala Val Arg Val Ala Gly Asp Lys Gln
    130                 135                 140

Ser Arg Gly Arg Gly Val Met Val Val Ile Asn Asp Arg Ile Gly Ser
145                 150                 155                 160
```

-continued

```
Ala Arg Tyr Ile Thr Lys Thr Asn Ala Ser Thr Leu Asp Thr Phe Arg
                165                 170                 175

Ala Asn Glu Glu Gly Tyr Leu Gly Val Ile Ile Gly Asn Arg Ile Tyr
            180                 185                 190

Tyr Gln Asn Arg Ile Asp Lys Leu His Thr Thr Arg Ser Val Phe Asp
        195                 200                 205

Val Arg Gly Leu Thr Ser Leu Pro Lys Val Asp Ile Leu Tyr Gly Tyr
    210                 215                 220

Gln Asp Pro Glu Tyr Leu Tyr Asp Ala Ala Ile Gln His Gly Val
225             230                 235                 240

Lys Gly Ile Val Tyr Ala Gly Met Gly Ala Gly Ser Val Ser Val Arg
                245                 250                 255

Gly Ile Ala Gly Met Arg Lys Ala Leu Glu Lys Gly Val Val Val Met
                260                 265                 270

Arg Ser Thr Arg Thr Gly Asn Gly Ile Val Pro Pro Asp Glu Glu Leu
            275                 280                 285

Pro Gly Leu Val Ser Asp Ser Leu Asn Pro Ala His Ala Arg Ile Leu
            290                 295                 300

Leu Met Leu Ala Leu Thr Arg Thr Ser Asp Pro Lys Val Ile Gln Glu
305                 310                 315                 320

Tyr Phe His Thr Tyr
                325

<210> SEQ ID NO 15
<211> LENGTH: 18
<212> TYPE: PRT
<213> ORGANISM: Humicola insolens

<400> SEQUENCE: 15

Met Lys Phe Phe Thr Thr Ile Leu Ser Thr Ala Ser Leu Val Ala Ala
1               5                   10                  15

Leu Pro
```

ASPARAGINASES

CROSS REFERENCE TO RELATED APPLICATIONS

This application is a continuation of U.S. application Ser. No. 12/613,983 filed on Nov. 6, 2009 (pending) which is a divisional of U.S. application Ser. No. 12/044,055 filed on Mar. 7, 2008 (now U.S. Pat. No. 7,666,652) which claims priority or the benefit under 35 U.S.C. 119 of European application no. 07103862.4 filed Mar. 9, 2007 and U.S. provisional application No. 60/894,316 filed Mar. 12, 2007, the contents of which are fully incorporated herein by reference.

FIELD OF THE INVENTION

The invention relates to new asparaginases having improved properties, preferably improved thermotolerance, such as improved activity at high temperatures and/or improved thermostability. The invention also relates to DNA sequences encoding such improved asparaginases, their production in a recombinant host cell, as well as methods of using the asparaginases, in particular for reduction of acrylamide in foods. The invention furthermore relates to methods of generating and preparing asparaginase variants having improved properties.

BACKGROUND OF THE INVENTION

It is known that acrylamide is formed in several food materials during heating to high temperatures. The acrylamide formation has been ascribed to a Maillard reaction wherein asparagine is one of the reactants. It is well known that acrylamide formation in heated food products may be reduced by a treatment reducing the amount of asparagine in the food materials, such as by subjecting the food materials to the action of the enzyme asparaginase (see e.g. WO2004/026042 (Frito-Lay North America, Inc.)).

A number of microbial asparaginases have been identified; see e.g. WO2004/030468 (DSM) disclosing the sequence of an asparaginase derived from *Aspergillus niger*, or WO2004/032648 (Novozymes A/S) disclosing sequences of asparaginases derived from *Aspergillus oryzae* and *Penicillium citrinum*. WO2004/032648 also mentions the amino acid sequences of asparaginases from *Aspergillus fumigatus* and *Aspergillus nidulans*. The amino acid sequence of an asparaginase from *Aspergillus terreus* can be obtained from the UniProt database (accession no. q0cwj1).

The amino acid sequence and the crystal structure of an L-asparaginase from *Erwinia chrysanthemi* have been described (Jacek Lubkowski, Miroslawa Dauter, Khosrow Aghaiypour, Alexander Wlodawera and Zbigniew Dauter (2003) Atomic resolution structure of *Erwinia chrysanthemi* L-asparaginase. *Acta Cryst.* D, 59, 84-92).

A method for designing proteins with improved thermal stability using 3-isopropylmalate dehydrogenase from *Thermus thermophilus* as a model enzyme has been described (Watanabe, K. et al. (2006) *J. Mol. Biol.* 355, 664-674).

For some applications, asparaginases having improved properties are desired, such as asparaginases having improved thermotolerance, e.g. improved thermostability or improved activity at high temperatures.

It is an object of the present invention to provide alternative asparaginases, in particular novel asparaginases having improved properties. Such improved asparaginases are suitable for use, e.g. in the production of food products.

SUMMARY OF THE INVENTION

The present inventors have modeled the three-dimensional structure of an asparaginase from *Aspergillus oryzae* based on the published structure of a homologous enzyme from *Erwinia chrysanthemi*. Based on the modeled structure, the inventors have identified amino acid residues of relevance for improving the properties of the asparaginase, especially the thermotolerance.

Further, the present inventors have predicted an inferred ancestral asparaginase sequence and from this sequence identified further amino acid residues of relevance for improving the properties of an asparaginase, especially the thermotolerance.

Based on such structural and functional considerations, asparaginase variants were constructed having modified amino acid residues at the identified positions and having altered physiochemical properties, especially improved relative activity at high temperatures and/or improved thermostability.

Accordingly, the present invention relates to a method for preparing a polypeptide comprising:

(a) providing an amino acid sequence of a parent polypeptide having asparaginase activity;

(b) selecting at least one amino acid residue at a position in the sequence which corresponds to any of positions 54, 57, 68-74, 82-86, 88, 93-96, 102, 107, 111, 113, 115, 137, 139, 164, 165, 172, 176, 184-186, 194, 196, 201, 206, 209, 212, 214, 215, 219, 220, 223, 224, 226, 228, 231, 235, 246, 249, 255, 260, 262, 264, 266, 271, 275, 278-288, 290, 299, 306, 307, 309-321, 323, 325, 327-342, 349, 351, 353, 356-363, 365, 366 and/or 375 in SEQ ID NO: 1;

(c) modifying the sequence by substituting or deleting the selected amino acid residue or inserting one or more amino acid residues adjacent to the selected amino acid residue;

(d) producing a variant polypeptide having the modified sequence;

(e) testing the variant polypeptide for asparaginase activity and thermotolerance; and (f) selecting a variant polypeptide having asparaginase activity and higher thermotolerance compared to the parent polypeptide.

The invention also relates to thermotolerant asparaginases, which may be obtained by such method.

Accordingly, the present invention relates to a polypeptide which:

(a) has asparaginase activity;

(b) has at least 70% identity to amino acids 80 to 378 of SEQ ID NO: 1; and (c) shows a residual asparaginase activity after heat treatment of at least 50% of the asparaginase activity without heat treatment, where heat treatment is incubation at pH 6 at a temperature of at least 64° C. for 20 minutes.

The present invention also relates to a polypeptide which:

(a) has asparaginase activity;

(b) has at least 70% identity to amino acids 80 to 378 of SEQ ID NO: 1; and (c) shows an asparaginase activity at pH 6 which is at least 25% higher at 65° C. than at 37° C.

In other aspects, the invention relates to novel asparaginases comprising differences in the amino acid sequence compared to SEQ ID NO: 1 at positions identified as being of relevance for improving the thermotolerance of the enzyme.

Accordingly, the present invention in one aspect relates to a polypeptide which:

(a) has asparaginase activity;

(b) has at least 80% identity to amino acids 80 to 378 of SEQ ID NO: 1; and (c) comprises an amino acid difference compared to SEQ ID NO: 1 at a position corresponding to any of positions 54, 57, 68-74, 82-86, 88, 93-96, 102, 107, 111, 113, 115, 137, 139, 164, 165, 172, 176, 184-186, 194, 196, 201, 206, 209, 212, 214, 215, 219, 220, 223, 224, 226, 228, 231, 235, 246, 249, 255, 260, 262, 264, 266, 271, 275, 278-288, 290, 299, 306, 307, 309-321, 323, 325, 327-342, 349, 351, 353, 356-363, 365, 366 and/or 375 in SEQ ID NO: 1.

In another aspect, the invention relates to a polypeptide which:

(a) has asparaginase activity;

(b) has at least 60% identity to amino acids 80 to 378 of SEQ ID NO: 1; and (c) comprises an amino acid difference compared to SEQ ID NO: 1 at a position corresponding to any of positions 71-74, 82, 88, 111, 113, 137, 164, 176, 196, 206, 223, 226, 231, 246, 266, 275, 278-282, 288, 309, 312, 329-332, 341, 357-359 and/or 363 in SEQ ID NO: 1.

In another aspect, the invention relates to a polypeptide which:

(a) has asparaginase activity;

(b) has at least 60% identity to amino acids 80 to 378 of SEQ ID NO: 1; and (c) comprises at least one of the following amino acid substitutions compared to SEQ ID NO: 1: 70H/K, 137S, 164D, 196I, 201Q, 278H/Q, 283C, 290V, 307A, 312Y, 334F, 336C/G/L, 337F/I, 366P and/or 375T; wherein each position corresponds to a position of amino acids 1 to 378 of SEQ ID NO: 1.

In another aspect, the invention relates to a polypeptide which:

(a) has asparaginase activity;

(b) has at least 50% identity to amino acids 80 to 378 of SEQ ID NO: 1; and (c) comprises an amino acid difference compared to SEQ ID NO: 1 at a position corresponding to any of positions 71-73, 82, 111, 137, 164, 176, 206, 223, 226, 231, 246, 266, 275, 279, 281, 288, 312, 329-332, 341, 357-359 and/or 363 in SEQ ID NO: 1.

And in yet another aspect, the invention relates to a polypeptide which:

(a) has asparaginase activity;

(b) has at least 50% identity to amino acids 80 to 378 of SEQ ID NO: 1; and (c) comprises at least one of the following amino acid substitutions compared to SEQ ID NO: 1: 70H, 137S, 164D, 196I, 201Q, 278H/Q, 283C, 290V, 307A, 312Y, 334F, 336C/G/L, 337F, 366P and/or 375T; wherein each position corresponds to a position of amino acids 1 to 378 of SEQ ID NO: 1.

The amino acid differences may be obtained by modifying a parent sequence, e.g., by site-directed mutagenesis. However, they may also be found in naturally occurring polypeptides, which are born with such amino acid differences compared to SEQ ID NO: 1.

The present invention also relates to isolated nucleic acid sequences encoding the asparaginases and to nucleic acid constructs, expression vectors, and host cells comprising the nucleic acid sequences as well as methods for producing and using the asparaginases.

In a still further aspect, the present invention provides a method of constructing a variant of a parent asparaginase, wherein the variant has at least one altered property as compared to the parent asparaginase, which method comprises:

(a) providing a structure of the parent asparaginase;

(b) analyzing the structure of the parent asparaginase to identify a structural part comprising at least one amino acid residue, which is of relevance for altering said property;

(c) constructing a variant of the parent asparaginase comprising a modification of at least one amino acid residue identified in (b) so as to alter said property; and (d) testing the resulting asparaginase variant for said property.

In a still further aspect, the present invention provides a method of constructing a variant of a parent asparaginase, wherein the variant has at least one altered property as compared to the parent asparaginase, which method comprises:

(a) providing a sequence of the parent asparaginase;

(b) aligning the sequence of the parent asparaginase with an inferred ancestral asparaginase sequence to identify at least one amino acid residue, which is of relevance for altering said property;

(c) constructing a variant of the parent asparaginase comprising a modification of at least one amino acid residue identified in (b) so as to alter said property; and (d) testing the resulting asparaginase variant for said property.

BRIEF DESCRIPTION OF THE FIGURES

FIG. 1 is a multiple alignment of asparaginases derived from *Aspergillus oryzae, Aspergillus fumigatus, Aspergillus nidulans, Penicillium citrinum, Aspergillus terreus* and *Aspergillus niger.*

FIG. 2 shows a parameter file for the Molecular Dynamics Simulation.

FIG. 3 shows a parameter file for the Molecular Dynamics Simulation.

DETAILED DESCRIPTION OF THE INVENTION

Novel Asparaginases

Figure 4:
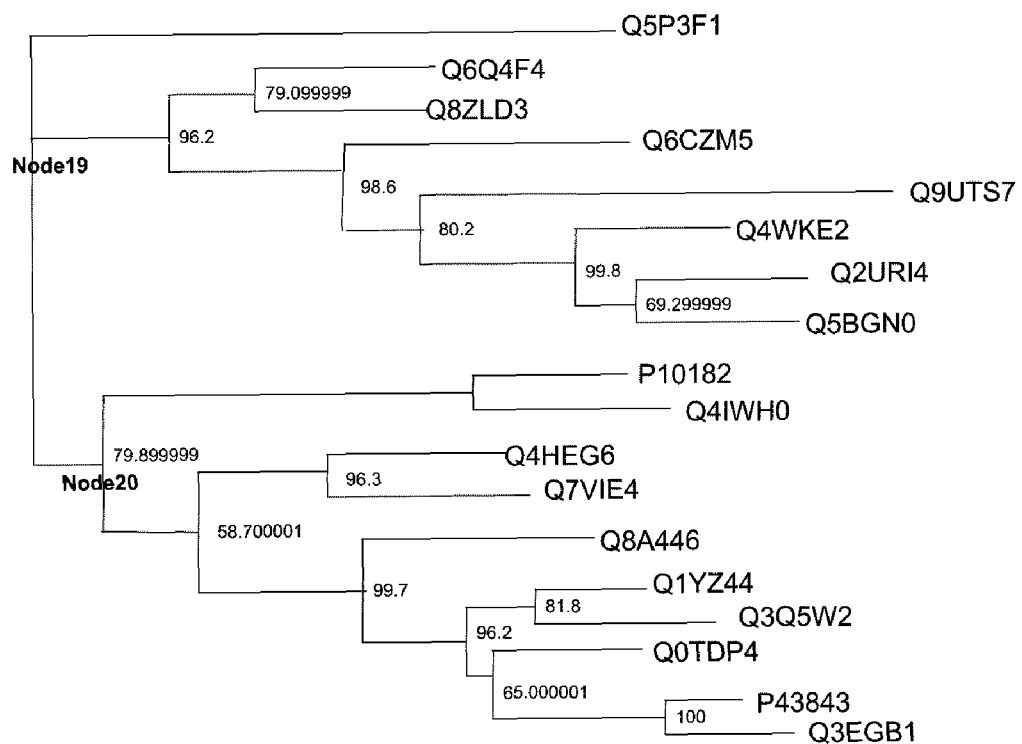
FIG. 4 shows a phylogenetic tree inferred by the maximum likelihood method applied in Example 6.

The polypeptides of the present invention have asparaginase activity. Preferably, they have amino acid sequences, which can be aligned with any of SEQ ID NOs: 1-6.

SEQ ID NO: 1 shows the amino acid sequence of an asparaginase from *Aspergillus oryzae* and the numbering system used in the context of the present invention. The amino acid sequence and the DNA sequence encoding it were previously published as SEQ ID NO: 2 and SEQ ID NO: 1 of WO2004/032648.

SEQ ID NO: 2 shows the amino acid sequence of an asparaginase from *Aspergillus niger*. The amino acid sequence and the DNA sequence encoding it were previously published as SEQ ID NO: 3 and SEQ ID NO: 2 of WO2004/030468.

SEQ ID NO: 3 shows the amino acid sequence of an asparaginase from *Aspergillus fumigatus* (previously published as SEQ ID NO: 6 of WO2004/032648). SEQ ID NO: 4 shows the amino acid sequence of an asparaginase from *Aspergillus nidulans* (previously published as SEQ ID NO: 4 of WO2004/032648). SEQ ID NO: 5 shows the amino acid sequence of an asparaginase from *Penicillium citrinum* (previously published as SEQ ID NO: 12 of WO2004/032648). SEQ ID NO: 6 shows the amino acid sequence of an asparaginase from *Aspergillus terreus* (obtained from the UniProt database, accession no. q0cwj1).

The polypeptides of the present invention may be partly or completely post-translationally processed. For instance, they may be N-terminally truncated at different positions, so that different N-terminal sequences will be found. The wild type *Aspergillus oryzae* asparaginase, when overexpressed in *Aspergillus oryzae*, has been found to be heterogeneously processed such that at least four N-terminal sequences were found in a purified sample, corresponding to polypeptides being truncated to amino acids 27-378, 30-378, 75-378 or 80-378. The polypeptides of the present invention may possibly be truncated at corresponding positions, or they may be truncated at other positions. The polypeptides of the present invention may thus, e.g., be truncated immediately before the position corresponding to any of positions 27, 30, 75 or 80 of SEQ ID NO: 1. In this context, what is meant by 'immediately before' is that truncation takes place at the N-terminal side of the position mentioned. The polypeptides of the present invention may thus have an N-terminal end corresponding, e.g., to any of positions 27, 30, 75 or 80 of SEQ ID NO: 1.

The polypeptides of the present invention may have an amino acid sequence having more than 50% identity to SEQ ID NO: 1, or a fragment thereof, preferably more than 60%, such as more than 70% or 80%, particularly more than 90%, especially more than 95%, e.g. more than 98%. The fragment of SEQ ID NO: 1 may, e.g., consist of amino acids 27-378, 30-378, 75-378 or 80-378.

In general, for the purpose of the present invention, when referring to a fragment of a polypeptide, what is meant is a polypeptide or chain of amino acids consisting of at least 100, such as at least 150 or at least 200 or 300, amino acids. A preferred fragment in the context of the present invention comprises or consists of the sequence of amino acids from the position corresponding to position 80 of SEQ ID NO: 1 to the C-terminal, e.g. amino acids 80-378 of SEQ ID NO: 1, amino acids 80-378 of SEQ ID NO: 2, amino acids 80-374 of SEQ ID NO: 3, amino acids 80-378 of SEQ ID NO: 4, amino acids 80-379 of SEQ ID NO: 5, or amino acids 80-375 of SEQ ID NO: 6.

In a preferred embodiment, the polypeptides of the present invention have an amino acid sequence having 1-50, such as 1-40, 1-30, 1-20 or 1-10 amino acid differences compared to SEQ ID NO: 1, or a fragment thereof.

In another aspect, the polypeptides of the present invention have an amino acid sequence having more than 50% identity to SEQ ID NO: 2, or a fragment thereof, preferably more than 60%, such as more than 70% or 80%, particularly more than 90%, especially more than 95%, e.g. more than 98%.

In yet another aspect, the polypeptides of the present invention have an amino acid sequence having more than 50% identity to any of SEQ ID NOs: 3-6, or a fragment thereof, preferably more than 60%, such as more than 70% or 80%, particularly more than 90%, especially more than 95%, e.g. more than 98%.

In a preferred aspect, the polypeptides of the present invention are eukaryotic, i.e. derived from, obtained from or originating from a eukaryotic organism. In a more preferred aspect, the polypeptides are derived from, obtained from or originating from *Aspergillus*.

The polypeptides of the present invention may show a high thermotolerance, e.g. they may have a high thermostability or a high relative asparaginase activity at high temperature.

In one aspect, the polypeptides of the present invention may be thermostable or have a high thermostability. The thermostability may be determined as the residual asparaginase activity after heat treatment divided by the asparaginase activity without heat treatment. Heat treatment may be incubation at pH 6 or around pH 6 at high temperature for, e.g., 10, 20, 30 or 40 minutes. The asparaginase activity without heat treatment may in this context be determined as the asparaginase activity of a sample which has been incubated at 4° C. in the same buffer and for the same time as the sample which is heat treated, or it may be the asparaginase activity before heat treatment.

The polypeptides of the present invention may show a residual asparaginase activity of at least 90%, such as at least 80%, at least 70%, at least 60%, at least 50% or at least 40%, after incubation at pH 6 at high temperature for a period of time, e.g. 20 minutes, compared to the asparaginase activity without heat treatment.

High temperature in the context of the present invention may mean, e.g., 55° C., 58° C., 60° C., 61° C., 62° C., 63° C., 64° C., 65° C., 66° C., 67° C., 68° C., 69° C., 70° C., 72° C. or 75° C.

The asparaginase activity may be determined by any method known in the art. It may be determined by incubating the enzyme with L-asparagine and hydroxylamine in a potassium phosphate buffer at pH 6 for 20 minutes followed by the coupling reaction with $FeCl_2$ and measuring A490, as described in Example 4. Incubation may be at any suitable temperature, e.g. 55° C.

In another aspect, the polypeptides of the present invention may have a high relative asparaginase activity at high temperature compared to at a reference temperature, e.g., 37° C., 40° C., 45° C. or 50° C. The asparaginase activity at high temperature and, e.g., 37° C. may be determined as described above, where the incubation with asparagine is performed at high temperature and 37° C., respectively. The asparaginase activity at high temperature divided by the activity at 37° C. may be at least 110%, preferably at least 120%, such as at least 125%, 130%, 140%, 150%, 170% or 200%, more preferably at least 250%, such as at least 300%, and even more preferably at least 500% or at least 700%.

In some aspects, the polypeptides of the present invention comprise an amino acid difference compared to a reference sequence, e.g. SEQ ID NO: 1, in one or more specified positions. Such positions may be identified by a method of the present invention. An amino acid difference in the context of the present invention may be deletion or substitution of the amino acid residue at the specified position or insertion of one or more additional amino acid residues adjacent to the amino acid residue at that position. Adjacent to means at either side, i.e. the insertion may be at the N-terminal or the C-terminal side of the amino acid residue at that position, i.e. immediately before or after the specified position. Substitution may mean substitution to another naturally occurring amino acid.

The amino acid difference may be naturally occurring, i.e. found in a naturally occurring wild-type asparaginase being less than 100% identical to SEQ ID NO: 1, or it may be introduced, e.g. by protein engineering, such as by site-directed mutagenesis, e.g. performed to improve the properties of a parent asparaginase.

The polypeptides of the present invention may be variants of a parent polypeptide, in which case an amino acid difference may refer to a difference in the amino acid sequence at a specific position in the variant, compared to the parent sequence. In that case, the amino acid difference may also be referred to as an amino acid modification.

The polypeptides of the invention, comprising amino acid differences at specified positions compared to SEQ ID NO: 1, or compared to a parent polypeptide, may comprise additional amino acid differences in addition to the amino acid differences described herein.

Parent Asparaginase

The parent polypeptide according to the present invention may be an asparaginase classified as EC 3.5.1.1 according to Enzyme Nomenclature (available at www.chem.qmul.ac.uk/iubmb/enzyme). It may be a eukaryotic asparaginase, e.g. a fungal asparaginase, such as a filamentous fungal asparaginase, e.g. native to a strain of *Aspergillus*, in particular *Aspergillus oryzae* or *Aspergillus niger*.

The parent asparaginase may have an amino acid sequence which is at least 50% (particularly at least 70%, at least 80%, at least 85%, at least 90%, at least 95% or at least 98%) homologous to any of SEQ ID NO: 1, SEQ ID NO: 2, SEQ ID NO: 3, SEQ ID NO: 4, SEQ ID NO: 5 or SEQ ID NO: 6. The parent asparaginase may particularly be one that can be aligned with any of these sequences. In a preferred aspect, the parent asparaginase may have the amino acid sequence of any of SEQ ID NO: 1, SEQ ID NO: 2, SEQ ID NO: 3, SEQ ID NO: 4, SEQ ID NO: 5 or SEQ ID NO: 6 or homologues of any of these. In a more preferred aspect, the parent asparaginase may have the amino acid sequence of SEQ ID NO: 1 or SEQ ID NO: 2 or homologues of any of these, preferably SEQ ID NO: 1.

Nomenclature for Amino Acid Differences

The specification and claims refer to amino acids by their one-letter codes. A particular amino acid in a sequence is identified by its one-letter code and its position, e.g. M1 indicates Met (methionine) at position 1, i.e. at the N-terminal.

The nomenclature used herein for defining substitutions is basically as described in WO 92/05249. Thus, G82P indicates substitution of G (Gly) at position 82 with P (Pro). D223N/L indicates substitution of D (Asp) at position 223 with N (Asn) or L (Leu). A plus-sign (+) between substitutions, e.g. 137S+228V means "and", i.e. that these two single substitutions are combined in one and the same asparaginase.

A substitution embraces a substitution into any one of the other nineteen natural amino acids, or into other amino acids, such as non-natural amino acids. For example, a substitution of amino acid T in position 71 includes each of the following substitutions: 71A, 71C, 71D, 71E, 71F, 71G, 71H, 71I, 71K, 71L, 71M, 71N, 71P, 71Q, 71R, 71S, 71V, 71W, and 71Y. These substitutions can also be designated T71A, T71C, T71D, etc. The same applies by analogy to each and every amino acid difference or amino acid substitution mentioned herein, to specifically include substitution to any other amino acid.

The parent polypeptide according to the present invention may be an asparaginase classified as EC 3.5.1.1 according to Enzyme Nomenclature (available at www.chem.qmul.ac.uk/iubmb/enzyme). It may be a eukaryotic asparaginase, e.g. a fungal asparaginase, such as a filamentous fungal asparaginase, e.g. native to a strain of *Aspergillus*, in particular *Aspergillus oryzae* or *Aspergillus niger*.

Insertion of an additional amino acid residue, e.g. Lys, at a specific position, e.g. after Gly at position 82, is designated, e.g., G82GK.

When designating a specific amino acid difference, the amino acid residue in the reference sequence may or may not be specified. For example, a substitution 96I indicates a substitution at the position corresponding to position 96 of e.g. SEQ ID NO: 1 to I (Ile) irrespective of which amino acid is present at position 96 in the reference sequence.

For purposes of the present invention, the alignment of two amino acid sequences can be determined by using the Needle program from the EMBOSS package (Rice, P. Longden, I. and Bleasby, A (2000) EMBOSS: The European Molecular Biology Open Software Suite. *Trends in Genetics* 16, (6) pp 276-277; emboss.org) version 2.8.0. The Needle program implements the global alignment algorithm described in Needleman, S. B. and Wunsch, C. D. (1970) *J. Mol. Biol.* 48, 443-453. The substitution matrix used is BLOSUM62, gap opening penalty is 10, and gap extension penalty is 0.5.

Wunsch, C. D. (1970) *J. Mol. Biol.* 48, 443-453. The substitution matrix used is BLOSUM62, gap opening penalty is 10, and gap extension penalty is 0.5.

The degree of identity between two amino acid sequences is calculated as the number of exact matches in an alignment of the two sequences, divided by the length of the shortest of the two sequences. The result is expressed in percent identity.

For the purpose of the present invention, an alignment of two or more sequences can be used to identify in one sequence the position corresponding to (i.e. being equivalent to) a specific position in another sequence, e.g. a reference sequence, e.g. SEQ ID NO: 1. If a position corresponding to a specific position of SEQ ID NO: 1 is to be identified in any of SEQ ID NOs: 2-6, the alignment shown in FIG. 1 can be used. 1. If a position corresponding to a specific position of SEQ ID NO: 1 is to be identified in any other homologous sequence, an alignment between SEQ ID NO: 1 and the homologous sequence is to be made as described above, and from this alignment each amino acid residue in the homologous sequence can be assigned a number corresponding to its equivalent amino acid residue in SEQ ID NO: 1. In this context, a homologous sequence is a sequence which can be aligned with SEQ ID NO: 1.

For the vast majority of amino acid residues in the polypeptides of the invention, and/or for use according to the invention, it is possible to directly and unambiguously assign an amino acid residue in the sequence of amino acids 1 to 378 of SEQ ID NO: 1 to which it corresponds. The only exception is amino acid residues which are additional to amino acids 1 to 378 of SEQ ID NO: 1. For example, it can be seen in FIG. 1 that the amino acid sequence from *A. niger* has additional amino acids S, D, T and A between S338 and S339 of the *A. oryzae* sequence, where the numbering is according to SEQ ID NO: 1.

In the context of the present application, the amino acid residues of the polypeptides of the invention may be numbered according to SEQ ID NO: 1. If the polypeptides of the invention are variants of a parent polypeptide, the amino acid residues of the parent may also be numbered according to SEQ ID NO: 1, so that the position of each amino acid residue may be referred to by the number of its corresponding (equivalent) amino acid in SEQ ID NO: 1.

Methods for Designing Novel Asparaginase Variants

In one aspect, the present invention relates to a method of constructing a variant of a parent asparaginase, wherein the variant has at least one altered property as compared to the parent asparaginase.

In one embodiment, the invention relates to a method of constructing a variant of a parent asparaginase, wherein the variant has at least one altered property as compared to the parent asparaginase, which method comprises:

(a) providing a structure of the parent asparaginase;

(b) analyzing the structure of the parent asparaginase to identify a structural part comprising at least one amino acid residue, which is of relevance for altering said property;

(c) constructing a variant of the parent asparaginase comprising a modification of at least one amino acid residue identified in (b) so as to alter said property; and (d) testing the resulting asparaginase variant for said property.

In another embodiment, the invention relates to a method of constructing a variant of a parent asparaginase, wherein the variant has at least one altered property as compared to the parent asparaginase, which method comprises:

(a) providing a sequence of the parent asparaginase;

(b) aligning the sequence of the parent asparaginase with an inferred ancestral asparaginase sequence to identify at least one amino acid residue, which is of relevance for altering said property;

(c) constructing a variant of the parent asparaginase comprising a modification of at least one amino acid residue identified in (b) so as to alter said property; and (d) testing the resulting asparaginase variant for said property.

The parent asparaginase to be used in a method of the present invention may have an amino acid sequence which is at least 50% identical to SEQ ID NO: 1 or a fragment thereof, preferably at least 60%, 70% or 80% identical, more preferably at least 90% identical, such as at least 95% or at least 98% identical. The fragment of SEQ ID NO: 1 may, e.g., consist of amino acid residues 50-378 or 80-378 of SEQ ID NO: 1.

In another aspect, the parent asparaginase may have an amino acid sequence which is at least 50% identical to any one of SEQ ID NOs: 2-6 or a fragment of any one of these sequences, preferably at least 60%, 70% or 80% identical, more preferably at least 90% identical, such as at least 95% or at least 98% identical.

The modification of at least one amino acid residue is typically accomplished by suitable modifications of a DNA sequence encoding the parent polypeptide in question.

The at least one altered property in the above method of the present invention may be, e.g., stability, such as temperature stability or pH dependent stability; temperature or pH dependent activity; specific activity; substrate specificity; higher or lower optimum temperature; higher or lower temperature of inactivation; or an increased ability to reduce acrylamide formation during the production of foods.

The at least one altered property may preferably be a higher thermotolerance as compared to the thermotolerance of the parent asparaginase, such as a higher thermostability or a higher relative asparaginase activity at high temperature as compared to the parent asparaginase. More preferably, the at least one altered property may be a higher relative asparaginase activity than the parent enzyme at pH 6 at 65° C. compared to 37° C. Or it may be a higher asparaginase activity than the parent enzyme at pH 6 at 65° C. Or it may be a higher asparaginase activity than the parent enzyme after incubation at around pH 6 at a temperature of at least 64° C. for 20 minutes.

Thermostability and relative asparaginase activity at high temperature may be determined as described above in the section 'Novel Asparaginases'.

Methods for Designing Novel Asparaginase Variants Based on 3D Structure

The structure of the parent asparaginase to be applied in a method according to the invention may be provided by any means known in the art. It may be that the structure has already been determined and is known in the art, in which case it may be provided by referring to the literature. Otherwise, the structure may be determined by X-ray diffraction or NMR. Or it may be provided by modeling the parent asparaginase to be used according to the method of the invention on the structure of another asparaginase, the structure of which has been previously determined or modeled.

The published three-dimensional structure of the L-asparaginase from *Erwinia chrysanthemi* (Jacek Lubkowski, Miroslawa Dauter, Khosrow Aghaiypour, Alexander Wlodawera and Zbigniew Dauter (2003) Atomic resolution structure of *Erwinia chrysanthemi* L-asparaginase. *Acta Cryst. D*, 59, 84-92) was used to model the three-dimensional structure of the asparaginase from *Aspergillus oryzae*. The structure of other asparaginases may be modeled in an analogous way.

The 3D model of *Aspergillus oryzae* asparaginase was built using the "Nest" homology modelling tool (Petrey, D., Xiang, X., Tang, C. L., Xie, L., Gimpelev, M., Mitors, T., Soto, C. S., Goldsmith-Fischman, S., Kernytsky, A., Schlessinger, A., Koh, I. Y. Y., Alexov, E. and Honig, B. (2003) Using Multiple Structure Alignments, Fast Model Building, and Energetic Analysis in Fold Recognition and Homology Modeling. *Proteins: Struc., Func. and Genet.* 53:430-435). The A-chain structure of the *Erwinia chrysanthemi* asparaginase was used as a template. The alignment below was used as a basis for the model building. The first 49 amino acid residues of the *Aspergillus oryzae* asparaginase sequence were not included in the model. The complete tetrameric structure was modeled by aligning a copy of the *Aspergillus oryzae* asparaginase model to each of the monomers in the *Erwinia chrysanthemi* asparaginase structure.

```
>P1; Ao_asparaginase
sequence: Ao_asparaginase:::::::::
                                       (SEQ ID NO: 13)
TLPNVTIFATGGTIAGSSADNTATTGYKAGAVGIQTLIDAVPEMLNVANV
AGVQVTNVGSPDITSDILLRLSKQINEVVCNDPTMAGAVVTHGTDTLEES
AFFLDATVNCRKPVVIVGAMRPSTAISADGPLNLLQSVTVAASPKARDRG
ALIVMNDRIVSAFYASKTNANTVDTFKAIEMGNLGEVVSNKPYFFYPPVK
P-TGKTEVDIRNITSIPRVDILYSYEDMHNDTLYSAIDNGAKGIVIAGSG
SGSVSTPFSAAMEDITTKHNIPIVASTRTGNGEVPSSAESSQIASGYLNP
AKSRVLLGLLLAQGKSIEEMRAVFERIGVA
*

>P1; 1o7j
structure: 1o7j::A::A:
                                       (SEQ ID NO: 14)
KLPNIVILATGGTIAGSAATGTQTTGYKAGALGVDTLINAVPEVKKLANV
KGEQFSNMASENMTGDVVLKLSQRVNELLARD-DVDGVVITHGTDTVEES
AYFLHLTVKSDKPVVFVAAMRPATAISADGPMNLLEAVRVAGDKQSRGRG
VMVVINDRIGSARYITKTNASTLDTFRANEEGYLGVIIGNRIYYQNRIDK
LHTTRSVFDVRGLTSLPKVDILYGYQDDPEYLYDAAIQHGVKGIVYAGMG
AGSVSVRGIAGMRKALEKG-VVVMRSTRTGNGIVPPDEELPGLVSDSLNP
AHARILLMLALTRTSDPKVIQEYFHTY
*
```

In one embodiment of the method of the present invention, the parent asparaginase is modeled on the known structure of the L-asparaginase from *Erwinia chrysanthemi*. In other words, the known structure of the *Erwinia chrysanthemi* asparaginase, such as the A-chain structure of the *Erwinia chrysanthemi* asparaginase, is used as a template when modeling the structure of the parent asparaginase.

In another embodiment of the method of the present invention, the parent asparaginase is modeled on the modeled three-dimensional structure of amino acid residues 50-378 of SEQ ID NO: 1, where this structure is modeled as described above.

The analysis of the structure referred to in step (b) of a method of the invention may involve an analysis of the contemplated impact of the structure or part of the structure on the function of the enzyme. For example change in electrostatic properties, change in surface hydrophobicity or altered local dynamics. Such local changes may lead to altered physical properties of the enzyme, such as thermostability, stability in presence of other chemical components (e.g. surfactants), pH-profile, adsorption properties or solubility.

The structural part which is identified in step (b) of the method of the invention may be composed of one amino acid residue. However, in some cases the structural part comprises more than one amino acid residue. The structural part to be modified may comprise amino acids located at an interface between different subunits in a multimer, e.g. a dimer or a tetramer, in a loop structure, close to the substrate binding site, or the like. The structural part to be modified is preferably one which in the folded enzyme is believed to contribute to the temperature stability profile of the enzyme, or is otherwise responsible for the properties of the asparaginase.

Described in the following are specific concepts which may be applied in the method of the invention and specific suggestions of variants to be designed by use of the different concepts. Specific amino acid modifications are suggested mainly with a view to improving the activity at high temperatures and/or the thermostability; however the modifications may affect other properties as well.

Concept: Molecular Dynamics (MD) Simulation

Molecular Dynamics (MD) simulations are indicative of the mobility of the amino acids in a protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at e.g. different temperatures, the temperature related mobility of residues is simulated. Regions having the highest mobility or flexibility (here isotropic fluctuations) may be suggested for random mutagenesis. It is here understood that the high mobility found in certain areas of the protein, may be reduced by changes in these areas by substitution, insertion or deletion of one or more residues.

The modeled tetrameric structure of the asparaginase from *A. oryzae* was subjected to 2 ns of molecular dynamics simulation, at temperatures 300K, 400K and 500K. The GROMACS 3.3 molecular simulation package was used (D. van der Spoel, E. Lindahl, B. Hess, G. Groenhof, A. E. Mark and H. J. C. Berendsen (2005): GROMACS: Fast, Flexible and Free, *J. Comp. Chem.* 26 p. 1701-1718). The simulations were set up as follows:

1) The modeled tetrameric structure was converted to GROMACS topology, while care was taken to ensure that disulfide bridges were defined correctly. The OPLSAA force field was used.
2) 100 steps of steepest descents minimization were run to remove atom clashes, and correct bond lengths. See FIG. 2 for parameter file.
3) The structure was solvated in an 11×11×11 nm water box.
4) The solvated structure was minimized by 100 steps of steepest descents minimization. See FIG. 2 for parameter file.
5) 2 ns of NVT MD simulation were run at temperatures 300K, 400K and 500K. See FIG. 3 for parameter file.
6) For each run, the first 800 ps were discarded, and the root mean square deviation (rmsd) for each of the C-alpha atom coordinates were calculated for the last 1200 ps, using the "g-rmsf" tool of the GROMACS package.
7) The data were compared between the three simulation temperatures and between the four monomers of the structure. Molecular Dynamics simulation data for three simulation temperatures (300K, 400K, 500K) and for all four monomers of the modeled tetrameric structure of the asparaginase from *A. oryzae*. Residue ranges that have high rmsd (root mean square deviation) values (relative to the average value for that temperature) are identified as mobile regions and thus targets of interest for stabilizing mutations. Residue ranges that have high rmsd values (relative to the average value for that temperature) are identified as mobile regions and thus targets of interest for stabilizing mutations:

Peak 1: 68-74
Peak 2: 279-288
Peak 3: 309-319
Peak 4: 329-342
Peak 5: 356-363

One aspect of the present invention relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following regions: position 68-74, position 279-288, position 309-319, position 329-342, and/or position 356-363; wherein each position corresponds to a position of amino acids 1 to 378 of SEQ ID NO: 1.

Thus, the polypeptide of the present invention may comprise a difference in the amino acid sequence compared to SEQ ID NO: 1 at one or more of the following positions, wherein each position corresponds to a position in SEQ ID NO: 1: 68, 69, 70, 71, 72, 73, 74, 279, 280, 281, 282, 283, 284, 285, 286, 287, 288, 309, 310, 311, 312, 313, 314, 315, 316, 317, 318, 319, 329, 330, 331, 332, 333, 334, 335, 336, 337, 338, 339, 340, 341, 342, 356, 357, 358, 359, 360, 361, 362, and/or 363. In a preferred embodiment, the amino acid difference is a substitution.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Concept: "Electrostatic Happiness"

The charge network around a specific amino acid residue may be determined. This is particularly relevant for residues located on the surface. The "Electrostatic happiness" concept aims to replace charged residues, which are located in an electrostatically unfavorable environment, or to introduce charges in positions where the potential suggest that such a charge would be electrostatically favorable. Favorable conditions (=happy residues) are negatively charged residues where the electrostatic potential is positive or vice versa; unfavorable conditions (=unhappy residues) are when the residue charge has the same sign as the electrostatic potential. The concept has been described in literature (Jose M. Sanchez-Ruiz and George I. Makhatadze (2001): To charge or not to charge?, TRENDS in Biotechnology 19, pp. 132-135), but is here implemented using GROMACS:
1) The structure is converted to GROMACS topology, using the OPLSAA force field. This also applies partial charges to each atom. The partial charges are averaged over the atoms within each residue. This value will be zero for non-titratable residues.
2) The electrostatic potential at each atom position is computed using the GROMACS tool "genion". The potentials are averaged over the atoms within each residue.
3) For each residue, the "Electrostatic happiness" is defined as the averaged partial charge multiplied by the averaged electrostatic potential. A positive value indicates an unhappy residue, a negative value suggest a happy residue. The value will be zero for non-titratable residues.

Charge reversals (e.g. K to E) are in some cases feasible. In other cases, substitution to a structurally similar but neutral residue may be optimal. Specific mutations based on this concept are: Residues which are not at interfaces between monomers: R196E, K194E, D88N, E255Q, K290E, E311K (for those suggesting a charge reversal, a neutral residue may be optimal instead). Residues which are at interfaces between monomers: D111N, D206N, E235Q, R266L, D275N, E331Q.

One aspect of the present invention relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following positions: D88, D111, K194, R196, D206, E235, E255, R266, D275, K290, E311, E331; wherein each position corresponds to a position of amino acids 1 to 378 of SEQ ID NO: 1.

Preferably, the amino acid difference is a substitution. Therefore, in a preferred aspect, the polypeptide of the present invention comprises at least one of the following amino acid substitutions compared to SEQ ID NO: 1, wherein each position corresponds to a position in SEQ ID NO:1: D88N, D111N, K194E, R196E, D206N, E235Q, E255Q, R266L, D275N, K290E, E311K, E331Q.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Concept: Introduction of Proline Residues

Substitution to proline residues may be suggested at various positions based on phi/psi backbone angles and side chain clashes. Residues that may be substituted for proline was identified using the command SUGPRO from the program WHATIF (G. Vriend (1990): WHAT IF: A molecular modeling and drug design program, J. Mol. Graph. 8, p 52-56). An alternative method is described in patent no. EP0585285B1.

One aspect of the present invention relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following positions: G82, T113, I365, I83, N278, Q84, N70, E366, V164, A137, F306, D115, T85, T280, L201; wherein each position corresponds to a position of amino acids 1 to 378 of SEQ ID NO: 1.

Preferably, the amino acid difference is a substitution. Therefore, in a preferred aspect, the polypeptide of the present invention comprises at least one of the following amino acid substitutions compared to SEQ ID NO: 1, wherein each position corresponds to a position in SEQ ID NO:1: G82P, T113P, I365P, I83P, N278P, Q84P, N70P, E366P, V164P, A137P, F306P, D115P, T85P, T280P, L201P.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Concept: Symmetry Point Interactions

The tetrameric asparaginases have 3 axes of 2-fold symmetry. A model structure of the Aspergillus oryzae asparaginase shows that the tetrameric asparaginases have 3 axes of 2-fold symmetry. As the enzyme is a homotetramer, a residue located along one of these axes is in close contact with the corresponding residue in one of the other monomers, and the pattern is repeated at the other end of the symmetry axis in concern.

In this way, two sets of interactions between the monomers may be created by just one mutation. This is particularly true for disulfide bridges, which may be introduced by substituting or inserting just one cysteine residue. Also other types of interactions, such as hydrophobic or electrostatic contacts, may be introduced along the symmetry axes.

One aspect of the present invention relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following positions, wherein each position corresponds to a position of amino acids 1 to 378 of SEQ ID NO: 1: S176, D223, G231, P246, Y271, S283, G328 (substitution to C will potentially result in formation of one or more disulfide bridges); D223, K249, D286 (based on hydrophobic or electrostatic contacts).

Preferably, the amino acid difference is a substitution. Therefore, in a preferred aspect, the polypeptide of the present invention comprises at least one of the following amino acid substitutions compared to SEQ ID NO: 1, wherein each position corresponds to a position in SEQ ID NO:1: S176C; D223C; G231C; P246C; Y271C; S283C; G328C; D223N/L; K249V/I/L; D286R/N/L.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Concept: Helix Capping

The first residues in each end of a protein alpha helix, particularly at the N-terminal end, may be involved in backbone-sidechain hydrogen bonds, that are of importance for the stability of the protein (ref: Protein Science (1998), 7, p 21-38). Substitutions here may lead to an increase in the thermostability.

In the regions identified using Molecular Dynamics simulation, the following positions are particularly interesting for mutation, as one or more of the above mentioned concepts may be applied:

| Peak 1: | |
|---|---|
| N70 | (Negative potential, reasonable proline position) |
| D69 | (Unhappy Asp) |
| A72 | (Negative potential) |
| Peak 2: | |
| D279 | (Unhappy Asp) |
| D286 | (Unhappy Asp) |
| K290 | (Unhappy Lys) |
| T280 | (Helix capping) |
| L281 | (Helix capping) |
| N278 | (Negative potential) |
| S283 | (Symmetry point) |
| Peak 3: | |
| S307 | (Helix capping) |
| E311 | (Unhappy Glu) |
| D312 | (Unhappy Asp) |
| H317 | (Positive potential) |
| Peak 4: | |
| E337 | (Unhappy Glu) |
| A336 | (Reasonable Pro position) |
| Peak 5: | |
| Q361 | (Negative potential) |
| K363 | (Unhappy K, reasonable Pro position) |

One aspect of the present invention relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following positions, wherein each position corresponds to a position of amino acids 1 to 378 of SEQ ID NO: 1: N70; D69; A72; D279; D286; K290; T280; L281; N278; S283; S307; E311; D312; H317; E337; A336; Q361; and/or K363.

Preferably, the amino acid difference is a substitution. Therefore, in a preferred aspect, the polypeptide of the present invention comprises at least one of the following amino acid substitutions compared to SEQ ID NO: 1, wherein each position corresponds to a position in SEQ ID NO:1: N70P/R/K; D69R/K; A72R/K; D279N/V/R; D286N/V/R; K290E/L; T280D/E; L281D/E; N278H/Q/R/K; S307A/D/E; E311Q/I/R; D312Y/N/V/R; H317D/E; E337Q/R/K/I; A336P; Q361K/R; and/or K363P/Q/E/L.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Methods for Designing Novel Asparaginase Variants Based on Ancestral Reconstruction An inferred ancestral asparaginase sequence to be used in a method of the present invention can be predicted from the sequences of a set of homologous proteins, as described in the literature (Joseph W. Thornton: Resurrecting Ancient Genes: Experimental Analysis Of Extinct Molecules (2004), *Nature Reviews Genetics* 5, p 366-375; C. W. Cunningham, K. E. Omland & T. H. Oakley: Reconstructing ancestral character states: a critical reappraisal (1998), *Trends in Ecology and Evolution* 13, p 361-336). Depending on the number of sequences and their homology, the inferred ancestral sequence may be significantly different from each of these sequences, e.g. 40-90%. Hence a significant number of the amino acid residues differ between a protein and its inferred ancestral sequence.

To obtain a more thermostable protein, a number of amino acid residues of a protein can be substituted with the corresponding residues of the inferred ancestral sequence. Because of the large number of differences, a method for selecting the preferred residue positions for substitution is desired. One way is to identify regions, where most of the residues are the same in the protein and its predicted ancestor. Within this region, residues that do differ between the protein and its ancestor are selected for substitution.

Based on ancestral reconstruction, the present inventors have identified a number of asparaginase variants having increased thermostability.

One aspect of the present invention therefore relates to a polypeptide which:

(a) has asparaginase activity;

(b) has at least 50%, such as at least 60%, at least 70%, at least 80%, at least 85%, at least 90%, at least 95% or at least 98%, identity to amino acids 80 to 378 of SEQ ID NO: 1; and (c) comprises an amino acid difference compared to SEQ ID NO: 1 in at least one of the following positions: 54, 57, 70, 83, 84, 86, 93-96, 102, 107, 137, 139, 165, 172, 184-186, 209, 212, 214, 215, 219, 220, 224, 260, 262, 264, 266, 299, 318, 320, 321, 323, 325, 327, 349, 351, 353 and/or 356, wherein each position corresponds to a position of amino acids 1 to 378 of SEQ ID NO: 1.

Preferably, the amino acid difference is a substitution. Therefore, in a preferred aspect, the polypeptide of the present invention comprises at least one of the following amino acid substitutions compared to SEQ ID NO: 1, wherein each position corresponds to a position in SEQ ID NO:1: V54I, F57L, N70K, I83V, Q84D, L86P, M93L, L94K, N95D, V96L, V102D, V107I, A137I, V139I, I165L, S172A, L184Y, Q185N, S186A, V209G, F212R, A214V, S215T, A219T, N220T, T224A, N260K, T262D, I264L, R266K, S299N, N318G, P320V, I321V, A323R, T325S, T327V, A349Q, S351A, V353I and/or G356M.

In a more preferred aspect, a polypeptide of the present invention comprises at least one of the following amino acid substitutions compared to SEQ ID NO: 1, wherein each position corresponds to a position in SEQ ID NO: 1: V54I, F57L, N70K, I83V, Q84D, L86P, V102D, N260K, T262D, A323R, T327V, A349Q, S351A and/or V353I.

In an even more preferred aspect, a polypeptide of the present invention comprises at least one of the following amino acid substitutions compared to SEQ ID NO: 1, wherein each position corresponds to a position in SEQ ID NO: 1: N70K, A323R, T327V, A349Q, S351A and/or V353I.

In a preferred aspect, the polypeptide is a variant of a parent polypeptide. The parent polypeptide may be any asparaginase, e.g. one of the asparaginases having the sequences set forth in SEQ ID NOs: 1-6 or homologues thereof.

Polypeptides of particular interest have a combination of one or more of the above amino acid differences with any of the other amino acid differences disclosed herein.

Preferred Asparaginases

One aspect of the present invention relates to a polypeptide which:

(a) has asparaginase activity;

(b) has at least 50%, such as at least 60%, at least 70%, at least 80%, at least 90%, at least 95% or at least 98%, identity to amino acids 80 to 378 of SEQ ID NO: 1; and (c) comprises an amino acid difference compared to SEQ ID NO: 1 in at least one of the following positions: 54, 57, 68-74, 82-86, 88, 93-96, 102, 107, 111, 113, 115, 137, 139, 164, 165, 172, 176, 184-186, 194, 196, 201, 206, 209, 212, 214, 215, 219, 220, 223, 224, 226, 228, 231, 235, 246, 249, 255, 260, 262, 264, 266, 271, 275, 278-288, 290, 299, 306, 307, 309-321, 323, 325, 327-342, 349, 351, 353, 356-363, 365, 366 and/or 375, wherein each position corresponds to a position in SEQ ID NO: 1.

Preferably, the polypeptide comprises an amino acid difference compared to SEQ ID NO: 1 in at least one of the following positions: 54, 57, 70, 83, 84, 86, 102, 137, 164, 196, 201, 228, 260, 262, 278, 283, 290, 307, 312, 323, 327, 334, 336, 337, 349, 351, 353, 366 and/or 375, wherein each position corresponds to a position in SEQ ID NO: 1.

The polypeptide may comprise an amino acid substitution compared to SEQ ID NO: 1. Preferably, the polypeptide comprises at least one of the following substitutions compared to SEQ ID NO: 1: 54I, 57L, 69K/R, 70H/K/P/R/S, 72K/R, 82P, 83P/V, 84P/D, 85P, 86P, 88N, 93L, 94K, 95D, 96L, 102D, 107I, 111N, 113P, 115P, 137P/S/I, 139I, 164D/P, 165L, 172A, 176C, 184Y, 185N, 186A, 194E, 196E/I, 201P/Q, 206N, 209G, 212R, 214V, 215T, 219T, 220T, 223C/L/N, 224A, 228V, 231C, 235Q, 246C, 249I/L/V, 255Q, 260K, 262D, 264L, 266L/K, 271C, 275N, 278H/K/P/Q/R, 279N/R/V, 280D/E/P, 281D/E, 283C, 286L/N/R/V, 290E/L/V, 299N, 306P, 307A/D/E, 311I/K/Q/R, 312N/R/V/Y, 317D/E, 318G, 320V, 321V, 323R, 325S, 327V, 328C, 331Q, 334F, 336C/G/L/P, 337F/I/K/Q/R, 349Q, 351A, 353I, 356M, 361K/R, 363E/L/P/Q, 365P, 366P and/or 375T. More preferably, the polypeptide comprises at least one of the following substitutions compared to SEQ ID NO: 1: 54I, 57L, 70H/K/S, 83V, 84D, 86P, 102D, 137S, 164D, 196I, 201Q, 228V, 260K, 262D, 278H/Q, 283C, 290V, 307A, 312Y, 323R, 327V, 334F, 336C/G/L, 337F/I, 349Q, 351A, 353I, 366P and/or 375T. Even more preferably, the polypeptide comprises at least one, such as at least two, at least three, at least four or at least five, of the following substitutions compared to SEQ ID NO: 1: 70K, 323R, 327V, 349Q, 351A and/or 353I. Even more preferably, the polypeptide comprises the following substitutions compared to SEQ ID NO: 1: 70K, 323R, 327V, 349Q, 351A and 353I. Most preferably, the polypeptide has the same sequence as SEQ ID NO: 1, or a homologous sequence, except for the following substitutions: 70K, 323R, 327V, 349Q, 351A and 353I. The polypeptide may be a variant of a parent enzyme having the sequence of SEQ ID NO: 1 or a homologous sequence.

In one preferred aspect of the present invention, the polypeptide comprises an amino acid difference compared to SEQ ID NO: 1 at a position corresponding to any of positions 70, 137, 164, 196, 201, 228, 278, 290, 366 and/or 375 in SEQ ID NO: 1. Preferably, the polypeptide comprises at least one of the following substitutions: 70H/K/S, 137S, 164D, 196I, 201Q, 228V, 278H/Q, 290V, 366P and/or 375T. The polypeptide may have a high relative asparaginase activity at high temperature, as determined above in the section 'Novel Asparaginases'. If the polypeptide is a variant of a parent polypeptide, the variant polypeptide may have a higher relative asparaginase activity at high temperature as compared to the parent polypeptide.

Particularly preferred polypeptides according to the present invention comprise the following substitutions or sets of substitutions compared to SEQ ID NO: 1: 70H, 70S, 70K, 70K+278H, 70K+278H+196I, 70K+278H+201Q, 70K+283C, 137S, 137S+228V, 164D, 196I, 201Q, 278H, 278Q, 290V, 366P, and/or 366P+375T.

In another preferred aspect of the present invention, the polypeptide comprises an amino acid difference compared to SEQ ID NO: 1 in at least one of the following positions: 70, 283, 307, 312, 334, 336 and/or 337. Preferably, the polypeptide comprises at least one of the following substitutions: 70K, 283C, 307A, 312Y, 334F, 336C/G/L and/or 337F/I, wherein each position corresponds to a position of amino acids 1 to 378 of SEQ ID NO: 1. The polypeptide may have a high thermostability, as determined above in the section 'Novel Asparaginases'. If the polypeptide is a variant of a parent polypeptide, the variant polypeptide may have a higher thermostability as compared to the parent polypeptide.

Particularly preferred polypeptides according to the present invention comprise the following substitutions or sets of substitutions compared to SEQ ID NO: 1: 70K, 70K+307A+312Y, 70K+307A+312Y+336L+337F, 70K+307A+312Y+336L+337F+283C, 70K+307A+312Y+334F, 70K+307A+312Y+336G+337I, 70K+307A+312Y+283C, 70K+283C, 70K+336C+337F, 70K+307A, and/or 70K+312Y.

In another preferred aspect of the present invention, the polypeptide comprises an amino acid difference compared to SEQ ID NO: 1 at a position corresponding to any of positions 54, 57, 70, 83, 84, 86, 93-96, 102, 107, 137, 139, 165, 172, 184-186, 209, 212, 214, 215, 219, 220, 224, 260, 262, 264, 266, 299, 318, 320, 321, 323, 325, 327, 349, 351, 353 and/or 356 in SEQ ID NO: 1. Preferably, the polypeptide comprises at least one of the following substitutions: V54I, F57L, N70K, I83V, Q84D, L86P, M93L, L94K, N95D, V96L, V102D, V107I, A137I, V139I, I165L, S172A, L184Y, Q185N, S186A, V209G, F212R, A214V, S215T, A219T, N220T, T224A, N260K, T262D, I264L, R266K, S299N, N318G, P320V, I321V, A323R, T325S, T327V, A349Q, S351A, V353I and/or G356M compared to SEQ ID NO: 1. More preferably, the polypeptide comprises at least one of the following substitutions: V54I, F57L, N70K, I83V, Q84D, L86P, V102D, N260K, T262D, A323R, T327V, A349Q, S351A and/or V353I compared to SEQ ID NO: 1. Most preferably, the polypeptide comprises at least one, such as at least two, at least three, at least four or at least five, of the following substitutions: N70K, A323R, T327V, A349Q, S351A and/or V353 I compared to SEQ ID NO: 1. The polypeptide may have a high relative asparaginase activity at high temperature, as determined above in the section 'Novel Asparaginases'. If the polypeptide is a variant of a parent polypeptide, the variant polypeptide may have a higher relative asparaginase activity at high temperature as compared to the parent polypeptide.

Particularly preferred polypeptides according to the present invention comprise the following sets of substitutions compared to SEQ ID NO: 1: N70K+V54I+F57L, N70K+ N260K+T262D, N70K+A323R+T327V, N70K+A349Q+ S351A+V353I, N70K+I83V+Q84D+A323R+T327V, N70K+L86P+V102D+A323R+T327V, N70K+A323R+ T327V+A349Q+S351A+V353I, N70K+I83V+Q84D+ A323R+T327V+A349Q+S351A+V353I, and/or N70K+ V102D+A323R+T327V+A349Q+S351A+V353I.

Methods for Preparing Asparaginase Variants Based on Sequence

The specific amino acid positions identified herein as being of relevance for improving the thermotolerance of an asparaginase will be of relevance for improving the thermotolerance of any asparaginase the sequence of which can be aligned with SEQ ID NO: 1.

Therefore, in one aspect the present invention relates to a method for preparing a polypeptide comprising:

(a) providing an amino acid sequence of a parent polypeptide having asparaginase activity;

(b) selecting at least one amino acid residue at a position in the sequence which corresponds to any of positions 54, 57, 68-74, 82-86, 88, 93-96, 102, 107, 111, 113, 115, 137, 139, 164, 165, 172, 176, 184-186, 194, 196, 201, 206, 209, 212, 214, 215, 219, 220, 223, 224, 226, 228, 231, 235, 246, 249, 255, 260, 262, 264, 266, 271, 275, 278-288, 290, 299, 306, 307, 309-321, 323, 325, 327-342, 349, 351, 353, 356-363, 365, 366 and/or 375 in SEQ ID NO: 1;

(c) modifying the sequence by substituting or deleting the selected amino acid residue or inserting one or more amino acid residues adjacent to the selected amino acid residue;

(d) producing a variant polypeptide having the modified sequence;

(e) testing the variant polypeptide for asparaginase activity and thermotolerance; and (f) selecting a variant polypeptide having asparaginase activity and higher thermotolerance compared to the parent polypeptide.

The parent polypeptide preferably has a sequence which has at least 50% identity to SEQ ID NO:1, SEQ ID NO:2, SEQ ID NO:3, SEQ ID NO:4, SEQ ID NO:5, SEQ ID NO:6, or a fragment of any of these sequences, more preferably at least 60%, at least 70% or at least 80% identity, and even more preferably at least 90%, at least 95% or at least 98% identity.

Most preferably, the parent polypeptide has a sequence which comprises or consists of any of SEQ ID NOs: 1-6 or a fragment thereof. A preferred fragment consists of the amino acid sequence from the position corresponding to position 80 of SEQ ID NO: 1 to the C-terminal of the polypeptide.

A higher thermotolerance in the context of the present invention may mean a higher thermostability or a higher relative asparaginase activity at high temperature.

Thermostability and relative asparaginase activity at high temperature may be determined as described above in the section 'Novel Asparaginases'.

In a preferred aspect, the at least one amino acid residue selected has a position in the sequence which corresponds to any of positions 54, 57, 70, 83, 84, 86, 102, 137, 164, 196, 201, 228, 260, 262, 278, 283, 290, 307, 312, 323, 327, 334, 336, 337, 349, 351, 353, 366 and/or 375 in SEQ ID NO: 1.

In another preferred aspect, the sequence is modified by substituting the at least one selected amino acid residue. Preferably, the sequence is modified by introducing at least one of the following substitutions: 54I, 57L, 69K/R, 70H/K/ P/R/S, 72K/R, 82P, 83P/V, 84P/D, 85P, 86P, 88N, 93L, 94K, 95D, 96L, 102D, 107I, 111N, 113P, 115P, 137P/S/I, 139I, 164D/P, 165L, 172A, 176C, 184Y, 185N, 186A, 194E, 196E/ I, 201P/Q, 206N, 209G, 212R, 214V, 215T, 219T, 220T, 223C/L/N, 224A, 228V, 231C, 235Q, 246C, 249I/L/V, 255Q, 260K, 262D, 264L, 266L/K, 271C, 275N, 278H/K/P/Q/R, 279N/R/V, 280D/E/P, 281D/E, 283C, 286L/N/R/V, 290E/L/ V, 299N, 306P, 307A/D/E, 311I/K/Q/R, 312N/R/V/Y, 317D/ E, 318G, 320V, 321V, 323R, 325S, 327V, 328C, 331Q, 334F, 336C/G/L/P, 337F/I/K/Q/R, 349Q, 351A, 353I, 356M, 361K/ R, 363E/L/P/Q, 365P, 366P and/or 375T; wherein each position corresponds to a position of amino acids 1 to 378 of SEQ ID NO: 1. More preferably, the sequence is modified by introducing at least one of the following substitutions: 54I, 57L, 70H/K/S, 83V, 84D, 86P, 102D, 137S, 164D, 196I, 201Q, 228V, 260K, 262D, 278H/Q, 283C, 290V, 307A, 312Y, 323R, 327V, 334F, 336C/G/L, 337F/I, 349Q, 351A, 353I, 366P and/or 375T; wherein each position corresponds to a position of amino acids 1 to 378 of SEQ ID NO: 1.

In a more preferred aspect, the sequence is modified by introducing at least one, such as at least two, at least three, at least four or at least five, of the following substitutions: 70K, 323R, 327V, 349Q, 351A and/or 353I; wherein each position corresponds to a position of amino acids 1 to 378 of SEQ ID NO: 1. In a more preferred aspect, the sequence is modified by introducing the following substitutions: 70K, 323R, 327V, 349Q, 351A and/or 353I, possibly in combination with other substitutions; wherein each position corresponds to a position of amino acids 1 to 378 of SEQ ID NO: 1.

The modification of one or more amino acid residues to obtain a polypeptide of the present invention can be accomplished by any method known in the art, e.g. as described in WO 94/14963 or WO 94/14964 (Unilever). The following describes methods for the cloning of asparaginase-encoding DNA sequences, followed by methods for generating mutations at specific sites within the asparaginase-encoding sequence.

Cloning a DNA Sequence Encoding an Asparaginase

The DNA sequence encoding an asparaginase may be isolated from any cell or microorganism producing the asparaginase in question, using various methods well known in the art. First, a genomic DNA and/or cDNA library could be constructed using chromosomal DNA or messenger RNA from the organism that produces the asparaginase to be cloned. Then, if the amino acid sequence of the asparaginase is known, labeled oligonucleotide probes may be synthesized and used to identify asparaginase-encoding clones from a genomic library prepared from the organism in question. Alternatively, a labeled oligonucleotide probe containing sequences homologous to another known asparaginase gene could be used as a probe to identify asparaginase-encoding clones, using hybridization and washing conditions of lower stringency.

Yet another method for identifying asparaginase-encoding clones would involve inserting fragments of genomic DNA and/or cDNA into an expression vector, such as a plasmid, transforming an asparaginase-negative bacterial or fungal host with the resulting DNA library, and then plating the transformed cells onto an agar medium that allows clones expressing the asparaginase to be identified. Such a medium may, for example, contain asparagine as a sole nitrogen source, such that only cells with an active asparaginase gene will grow. Another medium may, for example, include asparagine and a pH indicator that shifts color in response to the increase in pH that occurs as ammonium is released from the asparagine by asparaginase.

Alternatively, if the amino acid sequence is known for the asparaginase or related asparaginases, degenerate DNA primers may be designed that will allow the direct amplification of the asparaginase from genomic DNA, or from DNA libraries.

Alternatively, the sequences can be determined for the clones in a gene library, or for a selected sub-set of those clones, and these sequences can be compared to known asparaginase sequences in order to identify novel sequences.

Alternatively, the DNA sequence encoding the enzyme may be prepared synthetically by established standard methods, e.g. the phosphoroamidite method described S. L. Beaucage and M. H. Caruthers, (1981), *Tetrahedron Letters* 22, p. 1859-1869, or the method described by Matthes et al., (1984), *EMBO J.* 3, pp. 801-805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), *Science* 239, pp. 487-491.

Construction of Asparaginase Variants

An asparaginase variant may be obtained by site-directed mutagenesis at selected positions (see below) or by localized random mutagenesis, i.e. by introduction of random amino acid residues in selected positions or regions of the parent polypeptide, e.g. as described in WO 95/22615.

Random mutagenesis is suitably performed either as localized or region-specific random mutagenesis in at least three parts of the gene translating to the amino acid sequence in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the asparaginase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent asparaginase in question. This may, e.g., be advantageous when certain regions of the enzyme have been identified to be of particular importance for a given property of the enzyme.

Site-Directed Mutagenesis

Once an asparaginase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the asparaginase-encoding sequence, is created in a vector carrying the asparaginase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), *Biotechnology* 2, pp. 636-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into asparaginase-encoding DNA sequences is described in Nelson and Long, (1989), *Analytical Biochemistry* 180, pp. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of Asparaginases

According to the invention, a DNA sequence encoding a polypeptide of the present invention, including a variant produced by methods described above, or by any alternative methods known in the art, can be expressed, in enzyme form, using an expression vector which typically may include various control sequences, e.g., a promoter, operator, ribosome binding site, translation initiation signal, and, in some cases, a repressor gene or various activator genes.

Expression Vector

The recombinant expression vector carrying the DNA sequence encoding an asparaginase of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

The expression vector of the invention may also comprise a suitable transcription terminator and, in eukaryotes, polyadenylation sequences operably connected to the DNA sequence encoding the asparaginase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding an asparaginase and optionally a promoter, terminator and/or other elements, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Host Cells

The cell of the invention, either comprising a DNA construct or an expression vector of the invention as defined above, is advantageously used as a host cell in the recombinant production of an asparaginase of the invention. The cell may be transformed with the DNA construct of the invention encoding the asparaginase, conveniently by integrating the DNA construct (in one or more copies) in the host chromosome. This integration is generally considered to be an advantage as the DNA sequence is thereby more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or Gram negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*.

The host cell may also be a filamentous fungus e.g. a strain belonging to a species of *Aspergillus*, particularly *Aspergillus oryzae* or *Aspergillus niger*, or a strain of *Fusarium*, such as a strain of *Fusarium oxysporum, Fusarium graminearum, Fusarium sulphureum, Fusarium trichothecioides, Fusarium bactridioides, Fusarium sambucinum, Fusarium roseum, Fusarium cerealis, Fusarium crokkwellense,* or *Fusarium venenatum*.

In a particular embodiment of the invention the host cell is a protease deficient or protease minus strain.

This may for instance be the protease deficient strain *Aspergillus oryzae* JaL 125 having the alkaline protease gene named "alp" deleted. This strain is described in WO 97/35956 (Novo Nordisk A/S).

Filamentous fungi cells may be transformed by a process involving protoplast formation and transformation of the protoplasts followed by regeneration of the cell wall in a manner known per se. The use of *Aspergillus* as a host micro-organism is described in EP 238 023 (Novo Nordisk A/S), the contents of which are hereby incorporated by reference.

Production of Asparaginases by Cultivation of Transformant

The invention relates, inter alia, to a method of producing an asparaginase of the invention, which method comprises cultivating a host cell under conditions conducive to the production of the asparaginase and recovering the enzyme from the cells and/or culture medium.

The medium used to cultivate the cells may be any conventional medium suitable for growing the host cell in question and obtaining expression of the asparaginase of the invention. Suitable media are available from commercial suppliers or may be prepared according to published recipes (e.g. as described in catalogues of the American Type Culture Collection).

The asparaginase secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Screening and Testing

Asparaginase variants produced by any of the methods described herein may be tested, either prior to or after purification, for asparaginase activity, e.g. in a screening assay which measures the ability of the variant to hydrolyze asparagine, e.g. at high temperature.

In order to perform such screening, a microorganism being transformed with a DNA sequence encoding a mutated asparaginase of interest, and having the ability to express it, is incubated in a suitable medium and under suitable conditions for secretion of the enzyme.

Screening for variants having increased thermostability may for instance be done by incubating the culture supernatant at elevated temperature (e.g. in the range from 50° C.-80° C., preferably at 60, 62, 64, 66, 68, and/or 70° C.) for a time period (e.g. from 5 to 30 minutes, such as for 20 minutes) and measuring the asparagine hydrolyzing activity at suitable temperature, e.g. 55° C.

Screening for variants having increased relative activity at high temperature as compared to e.g. 37° C. may for instance be done by measuring the asparagine hydrolyzing activity of the culture supernatant at both a suitable reference temperature (e.g. 37° C.) and at elevated temperature (e.g. in the range from 50° C.-80° C., preferably at 60, 62, 64, 66, 68, and/or 70° C.). The relative activity is determined as the asparagine hydrolyzing activity at elevated temperature divided by the activity at the reference temperature.

Measurement of the asparagine hydrolyzing activity may be performed by methods known in the art, e.g. as described in the Examples.

The clones encoding asparaginase variants having higher thermostability and/or higher relative activity at high temperature may be selected for confirmation of sequence and enzyme purification. Further testing in regard to other altered properties may be performed on purified variants in accordance with methods known in the art. Such altered properties include thermostability, temperature dependent activity, thermoinactivation, pH dependent activity, pH dependent stability, specific activity, or substrate specificity, and any other parameter of interest.

Production of Foods

Asparaginases according to the present invention may be suitable in the production of food products, such as thermally processed carbohydrate-containing foods. Such food products, including coffee, cereals, cookies, potato chips, crackers, french fries, breads and rolls, have been shown in many cases to contain acrylamide, which is considered as probably carcinogenic for animals and humans. Acrylamide may be formed when the amino acid asparagine is heated in the presence of a reducing sugar. Therefore, reduction of acrylamide in thermally processed foods can be achieved by adding an asparaginase of the present invention to a food material prior to heating.

A food material in the context of the present invention means any unprocessed or partly processed form of the food product that occurs during the production process prior to obtaining the final form of the food product.

One aspect of the present invention is therefore a method for reduction of acrylamide in a food product, wherein an asparaginase of the invention is added to a food material which is subsequently heated. The enzyme should be added in an amount that is effective in reducing the level of asparagine present in the food material to be heated.

Examples of food products in which the process according to the invention may be useful include any cereal based products, such as bread, pastry, cake, pretzels, bagels, cookies, gingerbread, gingercake, breakfast cereals and crispbread; any potato based products, such as french fries, pommes frites, potato chips or crisps, fabricated potato snacks and croquettes; and any coffee based products.

Preferred heating steps are those where at least a part of the food material, e.g. the surface of the food material, is exposed to temperatures at which the formation of acrylamide is promoted, e.g. 110° C. or higher, or 120° C. or higher. The heating step in the process according to the invention may be carried out in ovens, for instance at a temperature between 180-220° C., such as for the baking of bread and other bakery products, or in oil such as the frying of potato chips, for example at 160-190° C.

One preferred embodiment is a method for reduction of acrylamide in french fries or other fried vegetable-based food products. The vegetable food material, e.g. potatoes, may be contacted with an asparaginase according to the invention after or during blanching, prior to drying and par-frying, to produce a par-fried vegetable food material. The enzyme may also be added after par-frying. The par-fried vegetable food material is preferably subjected to a final fry to produce a fried vegetable food product, or it is frozen to produce a frozen par-fried vegetable food material, which e.g. after freeze storage may be subjected to a final fry to produce a fried vegetable food product, e.g. french fries. The contacting with the asparaginase of the present invention is preferably accomplished by dipping, soaking or coating the vegetable food material in an aqueous enzyme solution or a mixture containing said enzyme.

EXAMPLES

Materials and Methods

Strains and Plasmids

E. coli DH12S (available from Gibco BRL) was used for yeast plasmid rescue.

pJN001 N2 is an S. cerevisiae and E. coli shuttle vector under the control of TPI promoter, constructed from pJC039 described in WO 01/92502, in which the Aspergillus oryzae asparaginase gene has been inserted.

Saccharomyces cerevisiae YNG318: MATa Dpep4[cir+] ura3-52, leu2-D2, h is 4-539 was used for asparaginase variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar and $H_2O$ (approx. 761 ml) is autoclaved together, and the separately sterilized SC-glucose solution added to the agar solution.

YPD: Bacto peptone 20 g/l, yeast extract 10 g/l, 20% glucose 100 ml/l.

PEG/LiAc solution: 40% PEG4000 50 ml, 5M Lithium Acetate 1 ml

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (eds.).

Yeast Transformation

Yeast transformation was carried out by lithium acetate method. Mix 0.5 microL of vector (digested by restriction endnucleases) and 1 microL of PCR fragments. Thaw YNG318 competent cells on ice. Mix 100 microL of the cells, the DNA mixture and 10 microL of carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to make colonies. Yeast total DNA was extracted by the Robzyk and Kassir's method described in Nucleic acids research vol. 20, No. 14 (1992) 3790.

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Example 1

Construction of Asparaginase Expression Vector

The Aspergillus oryzae asparaginase gene (SEQ ID NO: 1) was amplified with the primer pair Cutipre-asparaN2 F (SEQ ID NO: 7) and AsparaC R (SEQ ID NO: 8). The resulting PCR fragments were introduced into S. cerevisiae YNG318 together with the pJC039 vector digested with restriction enzymes to remove the mature part of Humicola insolens cutinase gene.

```
Cutipre-asparaN2 (41 mer)
                                         (SEQ ID NO: 7)
AGCCTTGTTGCTGCTCTCCCCGCCACAGACTCGAACGTCAC AsparaC R (50 mer)
                                         (SEQ ID NO: 8)
AGTCACCCTCTAGATCTCGACTTAATTAATCAAGCAACCCCAATCCGCTC
```

Plasmid, which is termed as pJN001N2, was recovered from the yeast transformants on SC-glucose plates and the internal sequence was determined to confirm the asparaginase gene. pJN001N2 thus has the signal sequence from *Humicola insolens* cutinase (MKFFTTILSTASLVAALP (SEQ ID NO: 15)) followed by the sequence of the mature part of *Aspergillus oryzae* asparaginase (amino acids 27-378 of SEQ ID NO: 1).

Example 2

Construction of Yeast Libraries and Site-Directed Variants

Libraries in yeast and site-directed variants were constructed by SOE PCR method (Splicing by Overlap Extension, see "PCR: A practical approach", p. 207-209, Oxford University press, eds. McPherson, Quirke, Taylor), followed by introduction of the purified PCR fragments mixed with vector digest into *Saccharomyces cerevisiae* for in vivo recombination.

Example 3

Library Screening (Relative Activity Selection)

Yeast clones/libraries were prepared as in Example 2, using pJN001N2 as a backbone. Clones on SC-glucose were inoculated to a well of a 96-well micro titre plate containing YPD medium and cultivated at 28° C. for 3 days. To determine the relative activity at a certain elevated temperature as compared to a reference temperature (37° C.), the asparagine hydrolyzing activity of the culture supernatant was measured at both 37° C. and the higher temperature (63° C. or 65° C.). The relative activity was determined as the asparagine hydrolyzing activity at elevated temperature divided by the activity at 37° C. The clones with higher relative activity were selected and the sequences were confirmed.
Reagents:
1M Potassium phosphate buffer (pH6.0)
1M KH$_2$PO$_4$(136 g/500 ml)+1M K$_2$HPO$_4$(174 g/500 ml)
Adjust to pH6.0
100 mM Potassium phosphate buffer (pH6.0)+0.1% tritonX-100 (1 L)
100 ml 1M Potassium phosphate buffer (pH6.0)
1 g Triton X-100
Adjust to 1000 ml
2M Hydroxylamine (HA) solution (100 ml)
13.9 g hydroxylamine
Adjust to 100 ml with 100 mM potassium phosphate buffer (pH6)
Stop solution (500 ml)
23.83 ml acetate
13.88 g FeCl$_3$ 6H$_2$O
84 ml 5N HCl
Adjust to 500 ml with H$_2$O
Substrate solution (100 ml)
10 ml 1 M Potassium phosphate buffer
0.5 g L-asparagine (132.12, final conc. 0.0325M)
5 ml 2M HA soln.
Adjust to 100 ml with H$_2$O.
Assay:

1 Pipette 20 microL sample into a well.

2 Add 100 microL of substrate solution into the well.

3 Incubate 20 minutes at 37° C. and higher.

4 Add 100 microL of stop solution into the well.

5 Measure A490 and determine the relative activity to 37° C. Results:

TABLE 1

Clone JN001N2 holds pJN001N2 encoding wild type *Aspergillus oryzae* asparaginase. In the other clones, the encoded asparaginase has the amino acid substitutions indicated.

| Clone# | Substitution | Relative activity 63° C./37° C. | 65° C./37° C. |
|---|---|---|---|
| JN002N2 | N70K | 732% | 661% |
| JN003N2 | A137S | 146% | 125% |
| JN007N2 | N278H | 127% | 107% |
| JN009N2 | E366P | 131% | 108% |
| JN010N2 | N70K + N278H | 635% | 557% |
| JN011N2 | N70K + N278H + R196I | 682% | 582% |
| JN012N2 | N70K + N278H + L201Q | 325% | 284% |
| JN018N2 | N70K + S283C | 350% | 271% |
| JN001N2 | wild type | 124% | 105% |

Example 4

Library Screening (Stability Selection)

Yeast clones/libraries were prepared as in Example 2, using pJN001N2 as a backbone. Clones on SC-glucose were inoculated to a well of a 96-well micro titre plate containing YPD medium and cultivated at 28° C. for 3 days. To determine the remaining activity after heat treatment, the asparagine hydrolyzing activity of the culture supernatant was measured at 55° C. after incubating for 20 minutes at elevated temperature (64° C. or 66° C., 4° C. as a reference). Then the clones with higher remaining activity were selected and the sequence was confirmed.
Reagents:
1M Potassium phosphate buffer (pH6.0)
1M KH$_2$PO$_4$ (136 g/500 ml)+1M K$_2$HPO$_4$(174 g/500 ml)
Adjust to pH6.0
100 mM Potassium phosphate buffer (pH6.0)+0.1% tritonX-100 (1 L)
100 ml 1M Potassium phosphate buffer (pH6.0)
1 g Triton X-100
Adjust to 1000 ml
2M Hydroxylamine (HA) solution (100 ml)
13.9 g hydroxylamine
Adjust to 100 ml with 100 mM potassium phosphate buffer (pH6)
Stop solution (500 ml)
23.83 ml acetate
13.88 g FeCl$_3$ 6H$_2$O
84 ml 5N HCl
Adjust to 500 ml with H$_2$O
Substrate solution (100 ml)
10 ml 1M Potassium phosphate buffer
0.5 g L-asparagine (132.12, final conc. 0.0325M)
5 ml 2M HA soln.
Adjust to 100 ml with H$_2$O
Assay:

1 Pipette 20 microL sample into a well.

2 Incubate the 96 well plate at appropriate temperature for 20 min. (4° C. for a control)

3 Add 100 microL of substrate solution into the well.

4 Incubate 20 min. at 55° C.

5 Add 100 microL of stop solution into the well.

6 Measure A490.
  Results:

TABLE 2

Clone JN001N2 holds pJN001N2 encoding wild type *Aspergillus oryzae* asparaginase. In the other clones, the encoded asparaginase has the amino acid substitutions indicated.

| | 4° C. 20 min (reference) | 64° C. 20 min | 66° C. 20 min | |
|---|---|---|---|---|
| JN001N2 | 100% | 34% | 4% | wild type |
| JN002N2 | 100% | 50% | 4% | N70K |
| JN055N2 | 100% | 68% | 8% | N70K + S307A + D312Y |
| JN056N2 | 100% | 85% | 32% | N70K + S307A + D312Y + A336L + E337F |
| JN057N2 | 100% | 85% | 69% | N70K + S307A + D312Y + A336L + E337F + S283C |
| JN030N2 | 100% | 71% | 10% | N70K + S307A + D312Y + S334F |
| JN031N2 | 100% | 85% | 35% | N70K + S307A + D312Y + A336G + E337I |
| JN032N2 | 100% | 81% | 52% | N70K + S307A + D312Y + S283C |
| JN018N2 | 100% | 69% | 12% | N70K + S283C |
| JN024N2 | 100% | 86% | 66% | N70K + A336C + E337F |
| JN025N2 | 100% | 65% | 11% | N70K + S307A |
| JN029N2 | 100% | 93% | 72% | N70K + D312Y |

Example 5

Saturation Libraries and Testing for Relative Activity

Saturation libraries were prepared as in Example 2. The backbone was JN001, which has an additional K226R mutation compared to JN001N2. Clones on SC-glucose were constructed as described in Example 2. Screening for increased relative activity was performed as described in Example 3. The table shows variants that performed better than JN001.

TABLE 3

Clone JN001N2 holds pJN001N2 encoding wild type *Aspergillus oryzae* asparaginase. In the other clones, the encoded asparaginase has the amino acid substitutions indicated.

| clone name | substitution | 65° C./37° C. |
|---|---|---|
| 2 | N70H + K226R | 215% |
| 3 | N70S + K226R | 117% |
| 4 | N70K + K226R | 302% |
| 37 | A137S + K226R + I228V | 65% |
| 42 | V164D + K226R | 96% |
| 52 | R196I + K226R | 39% |
| 56 | L201Q + K226R | 32% |
| 88 | K226R + N278H | 51% |
| 90 | K226R + N278Q | 32% |
| 103 | K226R + K290V | 45% |
| 131 | K226R + E366P + I375T | 39% |
| JN001 | K226R | 15% |
| JN001N2 | wild type | 122% |

Example 6

Construction of Site-Directed Variants Based on Ancestral Sequence Alignment

The 90 retrieved asparaginase sequences of Table 4 below were aligned with CLUSTAL X (Thompson, J. D., Gibson, T. J., Plewniak, F., Jeanmougin, F. & Higgins, D. G. (1997). The CLUSTAL_X windows interface: flexible strategies for multiple sequence alignment aided by quality analysis tools. *Nucleic. Acids Res.* 25, 4876-82.) using the default settings. The alignment was manually adjusted slightly.

TABLE 4

Retrieved asparaginase sequences

| Uniprot seq. no. | Sequence length | Organism |
|---|---|---|
| o25424 | 330 | *Helicobacter pylori* (*Campylobacter pylori*) |
| o34482 | 375 | *Bacillus subtilis* |
| o68897 | 362 | *Pseudomonas fluorescens* |
| p00805 | 348 | *Escherichia coli* |
| P06608 | 348 | *Erwinia chrysanthemi* |
| p10172 | 331 | *Acinetobacter glutaminasificans* |
| p10182 | 337 | *Pseudomonas sp* |
| p11163 | 362 | *Saccharomyces cerevisiae* |
| P38986 | 381 | *Saccharomyces cerevisiae* |
| p43843 | 349 | *Haemophilus influenzae* |
| P50286 | 330 | *Wolinella succinogenes* |
| P87015 | 360 | *Schizosaccharomyces pombe* |
| q0bep8 | 340 | *Burkholderia cepacia* |
| q0cwj1 | 375 | *Aspergillus terreus* |
| q0kyf3 | 352 | *Shewanella baltica* |
| q0pc96 | 331 | *Pseudomonas aeruginosa* |
| q0t0t1 | 348 | *Shigella flexneri* |
| q0tdp4 | 348 | *Escherichia coli* |
| q0z1e7 | 397 | *Acidovorax sp* |
| q13zi0 | 346 | *Burkholderia xenovorans* |
| q17xa3 | 350 | *Helicobacter acinonychis* str. Sheeba |
| q1ca77 | 345 | *Yersinia pseudotuberculosis* |
| q1cgg1 | 345 | *Yersinia pestis* |
| q1cte7 | 332 | *Bordetella avium* |
| q1ic27 | 362 | *Pseudomonas* |
| q1llw7 | 333 | *Ralstonia metallidurans* |
| q1r770 | 348 | *Escherichia coli* |
| q1vd62 | 354 | *Vibrio alginolyticus* |
| q1yz44 | 354 | *Photobacterium profundum* |
| q1zuu5 | 355 | *Vibrio angustum* |
| q2bxr2 | 355 | *Photobacterium sp* |
| q2l2r3 | 335 | *Bordetella avium* |
| q2uri4 | 378 | *Aspergillus oryzae* |
| q2wm94 | 336 | *Clostridium beijerincki* |
| q2xme2 | 362 | *Pseudomonas putida* |
| q31wl9 | 348 | *Shigella boydii* |
| q32c26 | 348 | *Shigella dysenteriae* |
| q39fj0 | 340 | *Burkholderia* sp. (strain 383) (*Burkholderia cepacia*) |
| q3egb1 | 349 | *Actinobacillus succinogenes* |
| q3kez6 | 362 | *Pseudomonas fluorescens* |
| q3nva7 | 316 | *Shewanella frigidimarina* |
| q3q5w2 | 385 | *Shewanella baltica* |
| q3yxe4 | 348 | *Shigella sonnei* |
| q4bpb5 | 340 | *Burkholderia vietnamiensis* |
| q4heg6 | 331 | *Campylobacter coli* |
| q4hj04 | 348 | *Campylobacter lari* |
| q4hpf7 | 346 | *Campylobacter upsaliensis* |
| q4hwj9 | 371 | *Gibberella zeae* (*Fusarium graminearum*) |
| q4iwh0 | 362 | *Azotobacter vinelandii* |
| q4kex6 | 362 | *Pseudomonas fluorescens* |
| q4wke2 | 379 | *Aspergillus fumigatus* |
| q57im4 | 347 | *Salmonella choleraesuis* |
| q57k10 | 348 | *Salmonella choleraesuis* |
| q5bgn0 | 378 | *Emericella nidulans* (*Aspergillus nidulans*). |
| q5hxc9 | 331 | *Campylobacter jejuni* |
| q5l874 | 352 | *Bacteroides fragilis* |
| q5nlv3 | 366 | *Zymomonas mobilis* |
| q5p3f1 | 361 | *Azoarcus sp* |
| q5pmk6 | 348 | *Salmonella paratyphi* |

TABLE 4-continued

Retrieved asparaginase sequences

| Uniprot seq. no. | Sequence length | Organism |
| --- | --- | --- |
| q63il0 | 351 | *Burkholderia pseudomallei* (*Pseudomonas pseudomallei*) |
| q64nh4 | 352 | *Bacteroides fragilis* |
| q65qv3 | 355 | *Mannheimia succiniciproducens* |
| q6bj17 | 396 | *Debaryomyces hansenii* (Yeast) (*Torulaspora hansenii*) |
| q6bxt9 | 331 | *Debaryomyces hansenii* (Yeast) (*Torulaspora hansenii*) |
| q6czm5 | 349 | *Erwinia carotovora* subsp. *atroseptica* |
| q6fal6 | 355 | *Acinetobacter* sp |
| q6li34 | 354 | *Photobacterium profundum* |
| q6q4f3 | 348 | *Erwinia chrysanthemi* |
| q6q4f4 | 346 | *Erwinia carotovora* |
| q74z49 | 388 | *Ashbya gossypii* (Yeast) (*Eremothecium gossypii*). |
| q7chj3 | 345 | *Yersinia pestis* |
| q7cpt7 | 348 | *Salmonella typhimurium* |
| q7vie4 | 378 | *Helicobacter hepaticus* |
| q7vnv6 | 349 | *Haemophilus ducreyi* |
| q7wwk9 | 349 | *Erwinia carotovora* |
| q83q85 | 348 | *Shigella flexneri* |
| q87j79 | 354 | *Vibrio parahaemolyticus* |
| q88k39 | 362 | *Pseudomonas putida* |
| q89kf7 | 379 | *Bradyrhizobium japonicum* |
| q8a446 | 352 | *Bacteroides thetaiotaomicron* |
| q8cvr4 | 348 | *Escherichia coli* |
| q8nkc0 | 360 | *Schizosaccharomyces pombe* |
| q8tff8 | 356 | *Schizosaccharomyces pombe* |
| q8xcu2 | 348 | *Escherichia coli* |
| q8xgy3 | 348 | *Salmonella typhi* |
| q8zld3 | 347 | *Salmonella typhimurium* |
| q9i407 | 362 | *Pseudomonas aeruginosa* |
| q9uts7 | 356 | *Schizosaccharomyces pombe* |
| q9zlb9 | 332 | *Helicobacter pylori* |
| p3jrh9 | 396 | *Burkholderia pseudomallei* |

Asparaginase phylogenetic tree was constructed by the neighbor-joining method. (Saitou, N.& Nei, M. (1987). The neighbor-joining method: a new method for reconstructing phylogenetic trees. *Mol. Biol. Evol.* 4, 406-425). Eighteen asparaginase sequences (Table 5) were selected for constructing a phylogenetic tree. These sequences were selected by removing the sequences with low homologies and avoiding repetition to cover as broad diversity as possible.

TABLE 5

Microbial asparaginases selected for reconstruction

| Uniprot seq. no. | Organism | Enzyme |
| --- | --- | --- |
| p10182 | *Pseudomonas* sp | ASPQ_PSES7. Glutaminase-asparaginase (EC 3.5.1.38) (L-asparagine/L-glutamineamidohydrolase) (L-ASNase/L-GLNase) (PGA). |
| q5p3f1 | *Azoarcus* sp | Q5P3F1_AZOSE. L-asparagine amidohydrolase (EC 3.5.1.1). |
| q6q4f4 | *Erwinia c carotovora* subsp. *atroseptica* | Q6Q4F4_ERWCH. L-asparaginase precursor. |
| q8zld3 | *Salmonella typhimurium* | Q8ZLD3_SALTY. Putative L-asparaginase (EC 3.5.1.1) (EC 1.6.4.2). |
| q6czm5 | *Erwinia carotovora* subsp. *atroseptica* | Q6CZM5_ERWCT. L-asparaginase II (EC 3.5.1.1). |
| q9uts7 | *Schizosaccharomyces pombe* | ASPG2_SCHPO. Probable L-asparaginase 2 precursor (EC 3.5.1.1) (L-asparagineamidohydrolase 2). |
| q4wke2 | *Aspergillus fumigatus* | Q4WKE2_ASPFU. L-asparaginase. |
| q2uri4 | *Aspergillus oryzae* | Q2URI4_ASPOR. Asparaginase. |
| q5bgn0 | *Emericella nidulans* (*Aspergillus nidulans*). | Q5BGN0_EMENI. Hypothetical protein. |
| q4iwh0 | *Azotobacter vinelandii* | Q4IWH0_AZOVI. L-asparaginase, type II precursor (EC 3.5.1.38). |
| q4heg6 | *Campylobacter coli* | Q4HEG6_CAMCO. L-asparaginase II (EC 3.5.1.1). |
| q7vie4 | *Helicobacter hepaticus* | Q7VIE4_HELHP. L-asparaginase (EC 3.5.1.1). |
| q8a446 | *Bacteroides thetaiotaomicron* | Q8A446_BACTN. L-asparaginase II. |
| q1yz44 | *Photobacterium profundum* | Q1YZ44_PHOPR. Putative periplasmic L-asparaginase II. |
| q3q5w2 | *Shewanella baltica* | Q3Q5W2_9GAMM. L-asparaginase, type II (EC 3.5.1.1). |
| q0tdp4 | *Escherichia coli* | Q0TDP4_ECOL5. L-asparaginase II (EC 3.5.1.1). |
| p43843 | *Haemophilus influenzae* | ASPG2_HAEIN. Probable L-asparaginase periplasmic precursor (EC 3.5.1.1) (L-asparagine amidohydrolase) (L-ASNase). |
| q3egb1 | *Actinobacillus succinogenes* | Q3EGB1_ACTSC. Asparaginase precursor (EC 3.5.1.1). |

After selecting well-aligned regions with GBLOCKS (Castresana, J. (2000). Selection of conserved blocks from multiple alignments for their use in phylogenetic analysis. *Mol. Biol. Evol.* 17, 540-52), the quartet-puzzling tree was inferred with Tree-Puzzle 5.0 (Schmidt, H. A., Strimmer, K., Vingron, M. & von Haeseler, A. (2002). TREE-PUZZLE: maximum likelihood phylogenetic analysis using quartets and parallel computing. *Bioinformatics* 18, 502-4). The maximum likelihood tree was then searched by the CODEML in PAML 3.13 (Yang, Z. (1997). PAML: a program package for phylogenetic analysis by maximum likelihood. *Comput. Appl. Biosci.* 13, 555-6) program package with the semi-automatic tree search option using the quartet-puzzling tree as the initial tree. The ancestral residues were then inferred with CODEML in PAML with the user-tree option, where the topology of the maximum likelihood tree (FIG. 4) was used. Then, node 19 and 20 were used as ancestral sequences inferred by the maximum likelihood method. The parsimony method with the software Bogen (Bogenpheil Co. Ltd.) was also used to infer ancestral sequences at the nodes node19 and node20 in the tree. These sequences are shown as V19 and V20 below.

The inferred ancestral sequences:

```
>node19
                                    (SEQ ID NO: 9)
PNIVILATGGTIAGAAASATVDTLIEAVPELKDLANVKGEQVANIGSEDM
NNEILLKLGIVITHGTDTLEETAYFLNLTVKSDKPVVLVGAMRPATAISA
DGPMNLYNAVAVAADKEARGKGVLVVMNDRIGSARYVTKTNTTTVDAFKA
PGYLGVIVNGKVYGGTRPHTTNSEFDVRKIDSLPKVDILYSYQNAAIDNG
AKGIVYAGTGNGSVSKRAKAGLKKAGIVVVRSSRVGNGLNPQKARILLML
ALTQT >node20
                                    (SEQ ID NO: 10)
PNIVILATGGTIAGAGASATVDTLIEAVPELKDLANVKGEQVANIGSEDM
NNEILLKLGIVITHGTDTLEETAYFLNLTVKSDKPVVLVGAMRPATAISA
DGPMNLYNAVAVAADKESRGKGVLVVMNDRIQSARYVTKTNTTNVDAFKS
PGPLGYIVNGKVYFFRSPHTTNSEFDVRKIDSLPKVDILYSYANALIDNG
AKGIVHAGTGNGSISKRLKDALKKAGIVVVRSSRVGQGLNPQKARILLML
ALTQT >V19
                                    (SEQ ID NO: 11)
MLALLSAAPALPNITILATGGTIAGAAASATQTTGYTAGAVGVDTLIAAV
PELKDLANVAGEQVANIDSEDITNAILLKLAKRVNALLADPDVDGIVITH
GTDTLEETAYFLNLTLKSAKPVVLVGAMRPATALSADGPLNLYNAVAVAA
DKAARGKGVLVAMNDRIGSARFVTKANTTDLDAFKAPEQGNLGAIANGKV
YFFTSPAKRHTLDSEFDRAIDSLPKVDILYDYQDADADAYDAAIDNGAKG
IVIAGSGNGSVSKRAKAAAKKAAKEGIIVVRSSRVGNGVVLDAADDAGVA
AGSLNPQKARILLMLALTKTKDPEEIQRYFDQY >V20
                                    (SEQ ID NO: 12)
MLLLAAPALPNITILATGGTIAGAGASATDTTGYTAGKVGVDTLIAAVPE
LKDLANVAGEQVANIDSEDITNEILLKLAKRVNALLDDPDVDGIVITHGT
DTLEETAYFLNLTLKSDKPVVLVGAMRPATALSADGPLNLYNAVAVAADK
AARGKGVLVAMNDRIGSARDVAKANTTDLDAFKSPFGPLGAIANGKVYFF
RSPAKRHTLDSEFDVRAIDSLPKVDILYSYANADADAYKALADNGAKGIV
HAGSGNGSVSKRAKAALKKAAKEGIIVVRSSRVNNGVLDAADDAKLGVAA
GDLNPQKARILLMLALTKTKDPKEIQRYFDEY
```

The positions for site-directed mutagenesis were selected by aligning these inferred ancestral sequences with the targeting asparaginase sequence (*Aspergillus oryzae* asparaginase). Site-directed variants were then constructed on the backbone JN002N2 as described in Example 3.

TABLE 6

The constructed ancestral site-directed variants

| Variant | Substitutions |
|---|---|
| JN034N2 | N70K V54I F57L |
| JN035N2 | N70K M93L L94K N95D V96L |
| JN036N2 | N70K A137I V139I |
| JN037N2 | N70K I165L |
| JN038N2 | N70K L184Y Q185N S186A |
| JN039N2 | N70K F212R A214V S215T |
| JN040N2 | N70K A219T N220T |
| JN041N2 | N70K T224A |
| JN042N2 | N70K N260K T262D |
| JN043N2 | N70K I264L R266K |
| JN044N2 | N70K S299N |
| JN045N2 | N70K N318G P320V I321V |
| JN046N2 | N70K A323R T327V |
| JN047N2 | N70K A349Q S351A V353I |
| JN048N2 | N70K G356M |
| JN058N2 | N70K I83V Q84D A323R T327V |
| JN059N2 | N70K L86P V102D A323R T327V |
| JN060N2 | N70K V107I A323R T325S T327V |
| JN061N2 | N70K S172A A323R T325S T327V |
| JN062N2 | N70K V209G A323R T325S T327V |
| JN063N2 | V54I F57L N70K A323R T325S T327V |
| JN064N2 | N70K N260K T262D A323R T325S T327V |
| JN065N2 | N70K A323R T327V A349Q S351A V353I |
| JN066N2 | V54I F57L N70K N260K T262D A323R T325S T327V A349Q S351A V353I |
| JN067N2 | N70K I83V Q84D A323R T327V A349Q S351A V353I |
| JN068N2 | N70K V102D A323R T327V A349Q S351A V353I |
| JN069N2 | I83VQ84D N70K V102D A323R T327V A349Q S351A V353I |

Example 7

Evaluation of Constructed Ancestral Site-Directed Variants

The site-directed variants of Example 6 were evaluated as described in Example 4 (except that the remaining activity after heat treatment was measured at 37° C. instead of 55° C.). JN001N2 was included, which holds pJN001N2 encoding wild type *Aspergillus oryzae* asparaginase. JN002N2 has the N70K substitution.

TABLE 7

Residual activity at 37° C. after incubating at said temperatures for 20 min. The activities are described as a relative value to the activity after incubation at 4° C.

|  | 4° C. | 64° C. | 66° C. | 68° C. | 70° C. | 72° C. | 74° C. |
|---|---|---|---|---|---|---|---|
| JN034N2 | 100% | 47% | 47% | 2% | −1% | | |
| JN042N2 | 100% | 78% | 27% | 0% | 0% | | |
| JN046N2 | 100% | 82% | 74% | 46% | 3% | | |
| JN047N2 | 100% | 71% | 66% | 10% | 0% | | |
| JN058N2 | 100% | | 80% | 50% | 8% | 1% | 0% |

TABLE 7-continued

Residual activity at 37° C. after incubating at said temperatures for 20 min. The activities are described as a relative value to the activity after incubation at 4° C.

| | 4° C. | 64° C. | 66° C. | 68° C. | 70° C. | 72° C. | 74° C. |
|---|---|---|---|---|---|---|---|
| JN059N2 | 100% | | 72% | 39% | 6% | | |
| JN065N2 | 100% | | 89% | 70% | 57% | 38% | 3% |
| JN067N2 | 100% | | | 73% | 61% | 32% | 6% |
| JN068N2 | 100% | | | 64% | 44% | 20% | 3% |
| JN002N2 | 100% | 64% | 12% | 6% | 3% | 1% | 2% |
| JN001N2 | 100% | | | 5% | 2% | 1% | 2% |

Example 8

Differential Scanning Calorimetry

Variants tested:
JN002N2Y is wild-type *Aspergillus oryzae* asparaginase having the following substitution: N70K, the variant being expressed from *S. cerevisiae*.
JN065N2Y is wild-type *Aspergillus oryzae* asparaginase having the following substitutions: N70K A323R T327V A349Q S351A V353I, the variant being expressed from *S. cerevisiae*.

Sample Preparation for Differential Scanning Calorimetry (DSC):
Approx. 1.5 ml of sample was transferred to a Slide-A-Lyzer® Dialysis Cassette (Pierce, cat. # 66380, 10 kDa MWCO) and dialyzed against 500 ml of 50 mM MES buffer pH 6.0 for 1-1½ hrs with magnetic stirring in a cold room (approx. 5° C.).
The buffer was changed to a fresh batch of 500 ml of 50 mM MES pH 6.0 and left to dialyze overnight.
The dialysis buffer was used for blanking in concentration determination by absorption measurement at 280 nm (A280) and as a reference for DSC.
The volume of the sample was adjusted using the dialysis buffer until an A280 of approx. 0.5-0.55 was obtained. Employing an extinction coefficient calculated based on amino acid sequence data (Vector NTI v. 9.0.0), this corresponds to an enzyme concentration of approx. 1.5-1.7 mg/ml.
The samples were degassed by vacuum suction and magnetic stirring for approx. 10 minutes prior to loading into the DSC apparatus.

DSC Data Recording and Processing:
Apparatus: VP-DSC (MicroCal™)
Scan interval: 20-80° C.
Scanrate: 60° C./h
Data processing software: MicroCal Origin© v. 4.10. The thermal denaturation temperature ($T_d$) was determined as the temperature corresponding to the apex of the signal in the thermogram. The data are summarised in Table 8 below.

TABLE 8

| Host cell | Enzyme | Buffer | Scanrate (° C./h) | Scan interval (° C.) | $T_d$ (° C.) | $A_{280}$ |
|---|---|---|---|---|---|---|
| S. cerevisiae | JN002N2Y | 50 mM MES pH 6.0 | 60 | 20-80 | 64 | 0.54 |

TABLE 8-continued

| Host cell | Enzyme | Buffer | Scanrate (° C./h) | Scan interval (° C.) | $T_d$ (° C.) | $A_{280}$ |
|---|---|---|---|---|---|---|
| S. cerevisiae | JN065N2Y | 50 mM MES pH 6.0 | 60 | 20-80 | 71 | 0.50 |

Example 9

Asparaginase Activity Assay

An asparaginase unit (ASNU) is defined as the amount of enzyme needed to generate 1.0 micromole of ammonia in 1 minute at 37° C. and pH 7.0.

Stock Solutions 50 mM Tris buffer, pH 7.0

189 mM L-Asparagine solution 1.5 M Trichloroacetic Acid (TCA)

Nessler's reagent, Aldrich Stock No. 34, 514-8 (Sigma-Aldrich)

Enzyme Reaction 500 microL buffer 100 microL L-asparagine solution 350 microL water are mixed and equilibrated to 37° C. 100 microL of enzyme solution is added and the reactions are incubated at 37° C. for 30 minutes. The reactions are stopped by placing on ice and adding 50 microL of 1.5M TCA. The samples are mixed and centrifuged for 2 minutes at 20,000 g.

Measurement of Free Ammonium 50 microL of the enzyme reaction mixture is mixed with 100 microL of water and 50 microL of Nessler's reagent, and absorbance measured at 436 nm after 1 minute.
Activity is compared to a known standard.

Example 10

Application Performance of the Thermostable Variant JN065N2 in Treatment of French Fries for Acrylamide Reduction Bintje potatoes (Grill-Kartoflen, Interfrugt Catering, Denmark) were manually peeled and cut into French fries using a French fry cutter (Taglia patate), size 0.8×0.8 cm. The potato sticks were divided into portions of 150 g (making sure that each portion consisted of sticks from different potatoes) and held in 400 ml de-ionized water until use. The potato sticks were blanched in two steps by dipping first in 4 L de-ionized water at 85° C. for 4 min and subsequently in 400 ml de-ionized water preheated to 70° C. for 15 minutes. Enzyme treatment was done by dipping the blanched potato sticks for 1 min at 40° C. in 300 ml enzyme solution (in deionised water) having 10,000 ASNU/L of the thermostable variant JN065N2 of Example 6 expressed from *Aspergillus oryzae*. For comparison a control sample with no enzyme treatment (fried right after blanching) was included. Samples were made in duplicate. After enzyme treatment the potato sticks were dried in a ventilated heating cupboard for 10 min at 85° C. and parfried in vegetable oil for 1 min at 175° C. The samples were blast frozen and finally second fried 3 min at 175° C.

The fries were blended and the acrylamide extracted using acetonitrile and an Automated Solvent Extractor (ASE from Dionex). The extract was treated with Carrez solution I and II, left overnight in the fridge and filtered using a 0.22 micrometer syringe filter before HPLC analysis (column: Dionex Ion-Pac ICE-AS1, 9×250 mm, eluent: 5 mM HCl, detection: UV 202 nm). Acrylamide was identified and quantified by comparing with known standards.

Results are given in Table 9 below.

TABLE 9

| Treatment | Acrylamide, ppb |
|---|---|
| Control | 1190 |
| JN065N2 | 600 |

Acrylamide in the final French fry product has been reduced by 50% showing that the enzyme is active in this application. For the wild-type enzyme typical reductions are around 50-60%, while a dip in water without enzyme results in approximately 25% reduction.

Example 11

Comparing Thermostability of the Variant JN065N2 and the Wt Enzyme in Continuous Treatment of French Fries for Acrylamide Reduction Bintje potatoes (Grill-Kartoflen, Interfrugt Catering, Denmark) were manually peeled and cut into French fries using a French fry cutter (Taglia patate), size 0.8×0.8 cm. The potato sticks were divided into portions of 150 g (making sure that each portion consisted of sticks from different potatoes) and held in 400 ml de-ionized water until use. The potato sticks were blanched in two steps by dipping first in 4 L de-ionized water at 85° C. for 4 min and subsequently in 400 ml de-ionized water preheated to 70° C. for 15 minutes. Enzyme treatment was done by holding the blanched potato sticks for 5 min at 60° C. in 1500 ml enzyme solution (in deionised water) having 10,000 ASNU/L of either the thermostable variant JN065N2 of Example 6 expressed from *Aspergillus oryzae* or the wt enzyme. Every 5 min a new portion of blanched potato sticks was dipped in the enzyme bath in order to mimic a continuous use of the enzyme bath. Samples from the enzyme bath were taken every 10-15 min for a total period of 2-3 hours and frozen for later activity analysis. Treated potatoes were discarded.

Results are shown in Table 10 below.

TABLE 10

| JN065N2 | | Wt enzyme | |
|---|---|---|---|
| Time (min) | % activity | Time (min) | % activity |
| 0 | 100 | 0 | 100 |
| 10 | 96 | 15 | 98 |
| 20 | 98 | 20 | 82 |
| 30 | 88 | 45 | 78 |
| 40 | 86 | 60 | 72 |
| 50 | 80 | 75 | 69 |
| 60 | 83 | 90 | 59 |
| 75 | 76 | 105 | 66 |
| 90 | 67 | 120 | 56 |
| 105 | 65 | 135 | 48 |
| 120 | 58 | 140 | 48 |
| 135 | 52 | | |
| 150 | 50 | | |
| 165 | 45 | | |
| 169 | 43 | | |

Upon fitting of the measured enzyme activities to an exponential decay curve, a half-life (T ½) of the enzyme can be estimated. For the wt enzyme T½ was 135 min and for the thermostable variant JN065N2 157 min, corresponding to a 16% increase.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A polypeptide which:
   (a) has asparaginase activity;
   (b) has at least 90% identity to amino acids 80 to 378 of SEQ ID NO: 1; and
   (c) comprises an amino acid difference compared to SEQ ID NO: 1 at a position corresponding to any of positions 83-84, 196, 226, 278, 290, 312, 336-337 and/or 366 in SEQ ID NO: 1.

2. The polypeptide of claim 1, wherein the amino acid difference is a substitution.

3. The polypeptide of claim 2, which comprises a substitution in at least one of the following positions: 196, 278, 290, 312, 336 and/or 366.

4. The polypeptide of claim 2, which comprises at least one of the following substitutions: 83PN, 84P/D, 196E/I, 278H/K/P/Q/R, 290E/L/V, 312N/R/V/Y, 336C/G/L/P, 337F/I/K/Q/R, and/or 366P.

5. The polypeptide of claim 2, which comprises at least one of the following substitutions: 83V, 84D, 196I, 278H/Q, 290V, 312Y, 336C/G/L, 337F/I and/or 366P.

6. The polypeptide of claim 1, which further comprises a substitution in at least one of the following positions: 54, 57, 68-74, 82, 85-86, 88, 93-96, 102, 107, 111, 113, 115, 137, 139, 164, 165, 172, 176, 184-186, 194, 201, 206, 209, 212, 214, 215, 219, 220, 223, 224, 228, 231, 235, 246, 249, 255, 260, 262, 264, 266, 271, 275, 279-281, 283, 286, 288, 299, 306, 307, 309-321, 323, 325, 327-335, 338-342, 349, 351, 353, 356-363, 365 and/or 375.

7. The polypeptide of claim 1, which further comprises a substitution at position 70.

8. The polypeptide of claim 6, which further comprises a substitution in at least one of the following positions: 54, 57, 86, 102, 137, 164, 201, 228, 260, 262, 283, 307, 323, 327, 334, 349, 351, 353 and/or 375.

9. The polypeptide of claim 6, which comprises at least one of the following substitutions: 54I, 57L, 69K/R, 70H/K/P/R/S, 72K/R, 82P, 85P, 86P, 88N, 93L, 94K, 95D, 96L, 102D, 107I, 111N, 113P, 115P, 137P/S/I, 139I, 164D/P, 165L, 172A, 176C, 184Y, 185N, 186A, 194E, 201P/Q, 206N, 209G, 212R, 214V, 215T, 219T, 220T, 223C/L/N, 224A, 228V, 231C, 235Q, 246C, 249I/L/V, 255Q, 260K, 262D, 264L, 266L/K, 271C, 275N, 279N/R/V, 280D/E/P, 281D/E, 283C, 286L/N/R/V, 299N, 306P, 307A/D/E, 311I/K/Q/R, 317D/E, 318G, 320V, 321V, 323R, 325S, 327V, 328C, 331Q, 334F, 349Q, 351A, 353I, 356M, 361K/R, 363E/L/P/Q, 365P and/or 375T.

10. The polypeptide of claim 6, which comprises at least one of the following substitutions: 54I, 57L, 70H/K/S, 86P, 102D, 137S, 164D, 201Q, 228V, 260K, 262D, 283C, 307A, 323R, 327V, 334F, 349Q, 351A, 353I and/or 375T.

11. The polypeptide of claim 6, which comprises one of the following substitutions: N70H, N70K or N70S.

12. The polypeptide of claim 6, which comprises the substitution N70K.

13. The polypeptide of claim 6, which comprises one of the following substitutions: 323R, 327V, 349Q, 351A and/or 353I.

14. The polypeptide of claim 1, which has at least 95% identity to amino acids 80 to 378 of SEQ ID NO: 1.

15. The polypeptide of claim 1, which has at least 98% identity to amino acids 80 to 378 of SEQ ID NO: 1.

16. An isolated nucleic acid sequence comprising a nucleic acid sequence which encodes the polypeptide of claim 1.

17. A nucleic acid construct comprising a nucleic acid sequence of claim 16 operably linked to one or more control sequences that direct the production of the polypeptide in a suitable expression host.

18. A recombinant expression vector comprising the nucleic acid construct of claim 17.

19. A recombinant host cell comprising the expression vector of claim 18.

20. A method for producing a polypeptide, the method comprising:
(a) cultivating the host cell of claim 19 to produce a supernatant comprising the polypeptide; and
(b) recovering the polypeptide.

21. A method for producing a food product, comprising:
(a) providing a food material; and
(b) treating the food material with the polypeptide of claim 1.

22. The method of claim 21, wherein the food material is heated after step (b).

23. The method of claim 21, wherein the method is for reduction of acrylamide in the food product.

24. The method of claim 21, wherein the food product is a cereal based product; a vegetable based product; or a coffee based product.

25. The method of claim 21, wherein the food product is bread, pastry, cake, pretzels, bagels, cookies, gingerbread, gingercake, breakfast cereals, crispbread, or a potato based product.

26. The method of claim 25, wherein the potato based product is french fries, potato chips or crisps, fabricated potato snacks or croquettes.

* * * * *